(12) United States Patent
Sauer et al.

(10) Patent No.: US 11,957,522 B2
(45) Date of Patent: Apr. 16, 2024

(54) DOCK FOR SURGICAL EQUIPMENT HOLDER

(71) Applicant: LSI Solutions, Inc., Victor, NY (US)

(72) Inventors: Jude S. Sauer, Pittsford, NY (US); Benjamin James Boseck, Canandaigua, NY (US); John F. Hammond, Canandaigua, NY (US); Angelo John Martellaro, Victor, NY (US); Matthew Wrona, Fairport, NY (US)

(73) Assignee: LSI Solutions, Inc., Victor, NY (US)

( * ) Notice: Subject to any disclaimer, the term of this patent is extended or adjusted under 35 U.S.C. 154(b) by 921 days.

(21) Appl. No.: 16/985,819

(22) Filed: Aug. 5, 2020

(65) Prior Publication Data
US 2021/0038343 A1 Feb. 11, 2021

Related U.S. Application Data

(60) Provisional application No. 62/882,667, filed on Aug. 5, 2019.

(51) Int. Cl.
*A61B 90/50* (2016.01)
*A61B 90/57* (2016.01)
(Continued)

(52) U.S. Cl.
CPC .............. *A61B 90/50* (2016.02); *A61B 90/57* (2016.02); *F16C 11/0695* (2013.01);
(Continued)

(58) Field of Classification Search
CPC ..... A61B 90/50; A61B 90/57; F16C 11/0695; F16M 11/14; F16M 11/2078; F16M 13/022; F16M 2200/066
(Continued)

(56) References Cited

U.S. PATENT DOCUMENTS

| 5,609,565 A | * | 3/1997 | Nakamura | ............. A61B 90/50 403/56 |
| D920,507 S | * | 5/2021 | Sauer | ............................ D24/133 |

(Continued)

FOREIGN PATENT DOCUMENTS

WO 2016160272 10/2016

OTHER PUBLICATIONS

Jul. 6, 2018 International Search Report; Copenheaver, Blaine R., International Search Report for PCT/US2018030846.
(Continued)

*Primary Examiner* — Muhammad Ijaz
(74) *Attorney, Agent, or Firm* — Michael E. Coyne

(57) ABSTRACT

A dock for a surgical equipment holder is disclosed. The dock for a surgical equipment holder includes a base having a central arm mount and a lower clamping jaw. The dock for a surgical equipment holder also includes an upper clamp jaw movably coupled to the base. The dock for a surgical equipment holder also includes a central docking arm coupled to the central arm mount and a central ball cup coupled to the to the central docking arm. The dock for a surgical equipment holder also includes a central attachment nut coupled to the central ball cup. The central attachment nut may include an extendable moment arm, and the dock may also include a ball coupled between the central ball cup and the central attachment nut and a surgical equipment holder attached to the ball.

21 Claims, 19 Drawing Sheets

(51) Int. Cl.
  *F16C 11/06* (2006.01)
  *F16M 11/14* (2006.01)
  *F16M 11/20* (2006.01)
  *F16M 13/02* (2006.01)
(52) U.S. Cl.
  CPC ......... *F16M 11/14* (2013.01); *F16M 11/2078* (2013.01); *F16M 13/022* (2013.01); *A61B 2090/571* (2016.02); *F16M 2200/066* (2013.01)
(58) Field of Classification Search
  USPC .... 248/276.1, 181.1, 181.2, 288.31; 602/35; 606/1
  See application file for complete search history.

(56) References Cited

U.S. PATENT DOCUMENTS

| | | | | |
|---|---|---|---|---|
| D949,331 S | * | 4/2022 | Sauer | D24/133 |
| D949,333 S | * | 4/2022 | Sauer | D24/133 |
| 2002/0077531 A1 | * | 6/2002 | Puchovsky | A61B 17/0206 600/232 |
| 2010/0178100 A1 | * | 7/2010 | Fricke | A61B 1/00149 403/90 |
| 2011/0190592 A1 | | 8/2011 | Kahle et al. | |
| 2013/0204262 A1 | * | 8/2013 | Menendez | A61B 17/02 606/89 |

OTHER PUBLICATIONS

Aug. 13, 2018 International Search Report; Young, Lee W., International Search Report for PCT/US2018033288.

Extended European Search Report for EP Application No. 20849653.9, filed Jan. 31, 2022, dated Jun. 9, 2023, 7 pages.

PCT International Search Report and Written Opinion for PCT/US2020/045002, filing date Aug. 5, 2020, dated Dec. 18, 2020, 11 pages.

* cited by examiner

DOCK FOR SURGICAL EQUIPMENT HOLDER

REFERENCE TO RELATED APPLICATIONS

This patent application claims priority to U.S. Provisional Patent Application No. 62/882,667 filed Aug. 5, 2019 and is entitled "DOCK FOR SURGICAL EQUIPMENT HOLDER." The entire 62/882,667 application is hereby incorporated by reference in their entirety.

FIELD

The claimed invention relates to surgical devices, and more specifically to a dock for surgical equipment holders.

BACKGROUND

Laparoscopic, endoscopic, and other types of minimally invasive surgical procedures often rely on percutaneous introduction of surgical instruments into an internal region of a patient where the surgical procedure is to be performed. Surgeons continue to find it desirable to utilize smaller and smaller access incisions in order to minimize trauma and reduce patient recovery times. Frequently, surgeons will make additional small incisions through which a viewing scope or other surgical equipment may be passed to assist in the operation. In the case of viewing scopes, an assistant may manipulate and/or hold the scope in a fixed position for the surgeon so that the surgeon may look at images, acquired by the scope, on a monitor screen in order to perform the minimally invasive operation. Equipment holders may be used in lieu of an assistant to position and hold surgical equipment such as, but not limited to, a viewing scope.

While surgical equipment holders are known to those skilled in the art, surgical equipment holders or docks for surgical equipment holders having the capability of mounting several, articulatable surgical equipment holders is desirable. The ability to adjust one or more surgical devices over multiple degrees of freedom may facilitate the use of multiple surgical devices including endoscopes, retractors, and the like, which are adjustable and mountable within an operating field on or around a surgical operating table, for example, on the rail of a surgical table or some other equipment in an operating room.

Other industries are also beset with the similar dilemma of having the capability to easily, reliably and adjustably mount one or more instruments or instrumentation holders. While instrumentation holders are known to those skilled in the art, easily adjustable mounts with enhanced mechanical function are not as prevalent. Therefore, it would be desirable to have a single docking station for adjustably mounting multiple surgical equipment holders.

Figure 1:
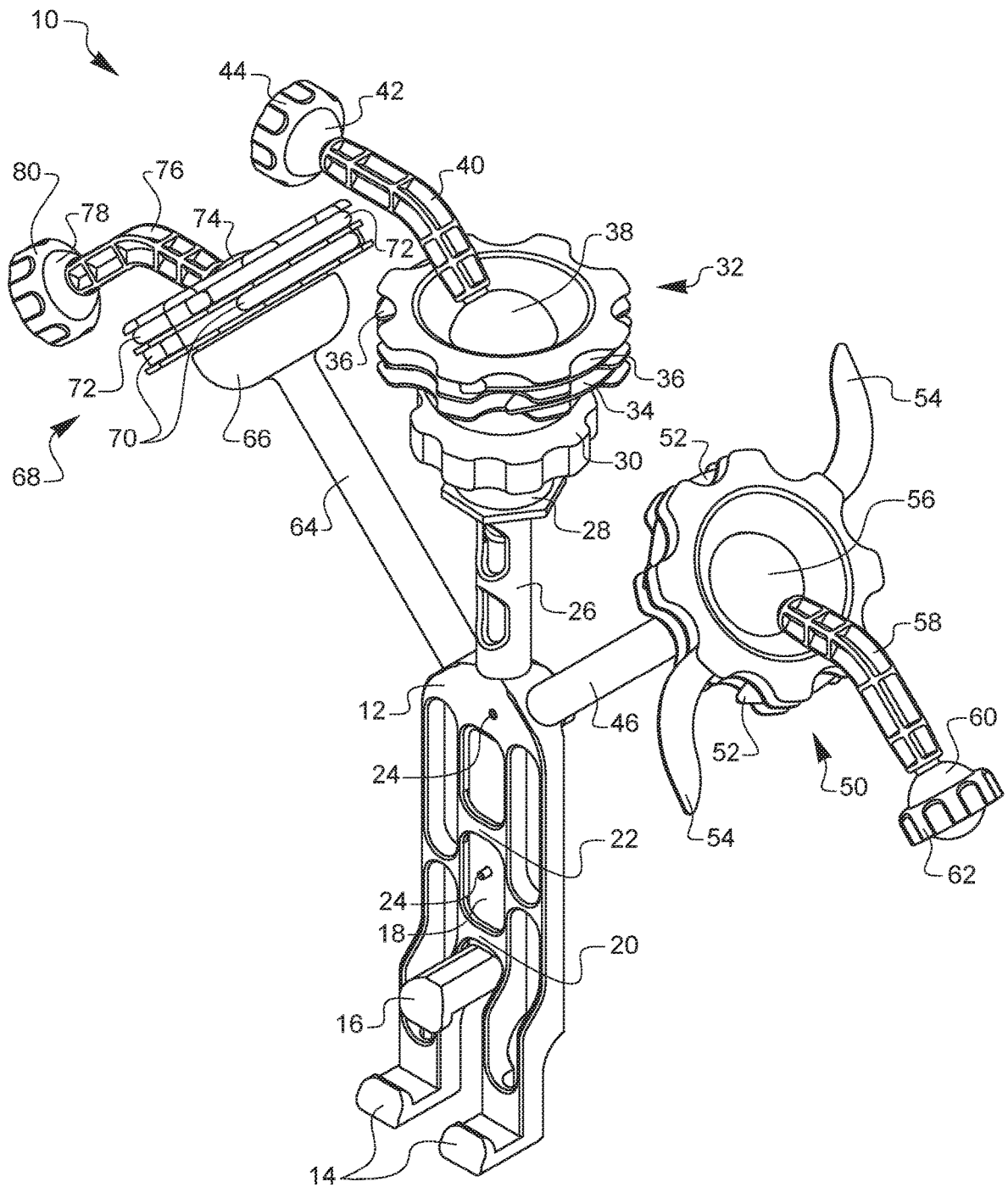
FIG. 1 is a top-right-front perspective view of one embodiment of a surgical equipment holder dock.

It will be appreciated that for purposes of clarity and where deemed appropriate, reference numerals have been repeated in the figures to indicate corresponding features, and that the various elements in the drawings have not necessarily been drawn to scale in order to better show the features.

SUMMARY

A dock for a surgical equipment holder a base is disclosed. The dock for a surgical equipment holder includes a base having a central arm mount, a side arm mount, and a lower clamping jaw. The dock for a surgical equipment holder also includes an upper jaw movably coupled to the base; and a central docking arm coupled to the central arm mount including an inner rod coupled to the upper jaw, a knob coupled to the inner rod, a hollow outer rod disposed over the inner rod, and a central ball cup coupled to the inner rod. The dock for a surgical equipment holder also includes an attachment nut coupled to the central ball cup.

Another embodiment of a dock for a surgical equipment holder is disclosed. The dock for a surgical equipment holder may include a central arm mount having a central docking arm coupled to the central arm mount having a central ball cup coupled to the central docking arm and a central attachment nut coupled to the central ball cup. The dock for a surgical equipment holder may also include a first side arm mount having a first side docking arm coupled to the first side arm mount having a first side ball cup coupled to the first side docking arm and a first side attachment coupled to the first side ball cup. A second side arm mount of the dock for a surgical equipment holder may include a second side docking arm coupled to the second side arm mount having a second side ball cup coupled to the second side docking arm and a second attachment nut coupled to the second side ball cup.

Another dock for a surgical equipment holder is disclosed, having a base which may include a central arm mount, a first side arm mount, a second side arm mount, and a lower clamping jaw. The dock for a surgical equipment holder may also include an upper jaw movably coupled to the base; and a central docking arm coupled to the central arm mount may include: an inner rod coupled to the upper jaw, a knob coupled to the inner rod, a hollow outer rod disposed over the inner rod, and a central ball cup coupled to the inner rod. The dock for a surgical equipment holder may also include a central attachment nut having an extendable moment arm, a ball pivotably held between the central ball cup and the central attachment nut, and a surgical equipment holder coupled to the ball.

DETAILED DESCRIPTION

FIG. 1 is a top-right-front perspective view of one embodiment of a surgical equipment holder dock. This embodiment of a surgical equipment holder dock 10 includes a base 12 which defines a pair of lower clamp jaws 14, a lower stop 20, and an upper stop 22. Internally movable within the base 12 of the surgical equipment holder dock 10 is an upper clamp jaw 16 connected to an upper clamp jaw shaft 18. The upper clamp jaw shaft 18 includes a stop pin 24 which is located on the upper clamp jaw shaft 18 such that the pin 24 is located between the lower stop 20 and the upper stop 22 and is configured to limit the vertical travel of the upper clamp jaw shaft 18 and therefore the relative position of the upper clamp jaw 16 in relation to the lower clamp jaws 14. Other embodiments may or may not include stop pins and may limit travel of the movable portion of the clamp jaws by means known to those skilled in the arts. Other embodiments may not limit travel at all. Other embodiments may have a movable lower clamp jaws or movable lower and upper clamp jaws. Other embodiments may have additional features on the inside portions or surfaces of the upper or lower clamp jaws, such as bevels or other textured features configured to improve consistent clamping forces to accommodate a variety of surgical rail shapes and sizes. The base 12 is configured to clamp the surgical equipment holder dock 10 to a surgical table rail. Attached to the upper portion of the base 12 is a central docking arm 26. This central docking arm 26 has a locking nut 28 attached to the top of the central docking arm 26. Above the locking nut 28 is a body lock knob 30, which is connected to the upper clamp jaw shaft 18 via an inner shaft or inner rod, which is not explicitly shown in this view, but will be discussed later. Above the body lock knob 30 is a central ball cup or socket, also not shown in this view but will be discussed later. A central attachment nut 32 is coupled to the socket. The attachment nut 32 includes two lower extendable moment arms 34 and two upper extendable moment arms 36. A large coupler ball 38 is held between the socket attached to the central docking arm 26 and the attachment nut 32. A bent coupler rod 40 is attached on one end to the large coupler ball 38 and attached to a small coupler ball 42 on the opposite end. Over the small coupler ball 42, a retainer ring 44 is connected, which will later serve as a mounting point for a surgical equipment holder, which is not shown in this view. In addition to the central docking arm 26, the surgical equipment holder dock 10 also has a first side docking arm 46 and a second side docking arm 64 attached to the base 12, each angled at an approximate angle of 45 degrees and in the same plane relative to the central docking arm 26. While a 45-degree angle is shown in this embodiments, other embodiments may have other angles of the side arm as compared to the central docking arm, as well as side arms not in the same plane as the central docking arm. The first side docking arm 46 defines a first side coupling ball cup 48, not visible in this view, which is configured to combine with a first side attachment nut 50 having two lower extendable moment arms 52 and two upper extendable moment arm 54. A large coupler ball 56 is held between the coupling ball cup 48 and the attachment nut 50. A bent coupler rod 58 is attached on one end to the large coupler ball 56 and attached to a small coupler ball 60 on the opposite end. Over the small coupler ball 60, a retainer ring 62 is connected, which will later serve as a mounting point for a surgical equipment holder, which is not shown in this view. The second side docking arm 64 also defines a second side coupling ball cup 66 which is configured to combine with a second side attachment nut 68 having two lower extendable moment arms 70 and two upper extendable moment arms 72. A large coupler ball 74 is held between the coupling ball cup 66 and the attachment nut 68. A bent coupler rod 76 is attached on one end to the large coupler ball 74 and attached to a small coupler ball 78 on the opposite end of the coupler rod 76. Over the small coupler ball 78, a retainer ring 80 is connected, which will later serve as a mounting point for a surgical equipment holder which is not shown in this view. The position of each of the coupler rods 40, 58, 76 can be positioned and locked by first loosening one of the attachment nuts 32, 50, 68 placing the position of the coupler rod 40, 58, 76 as desired, and therefore any attached fixturing or devices, such as surgical equipment holders. Next, the attachment nut 32, 50, 68 is tightened, thereby locking the coupler rod 40, 58, 76 into the desired position by clamping the large coupler ball 38, 56, 74 between the attachment nut 32, 50, 68 and each ball cup 128, 48, 66. An attachment nut may also be referred to as an attachment socket.

Figure 2A:
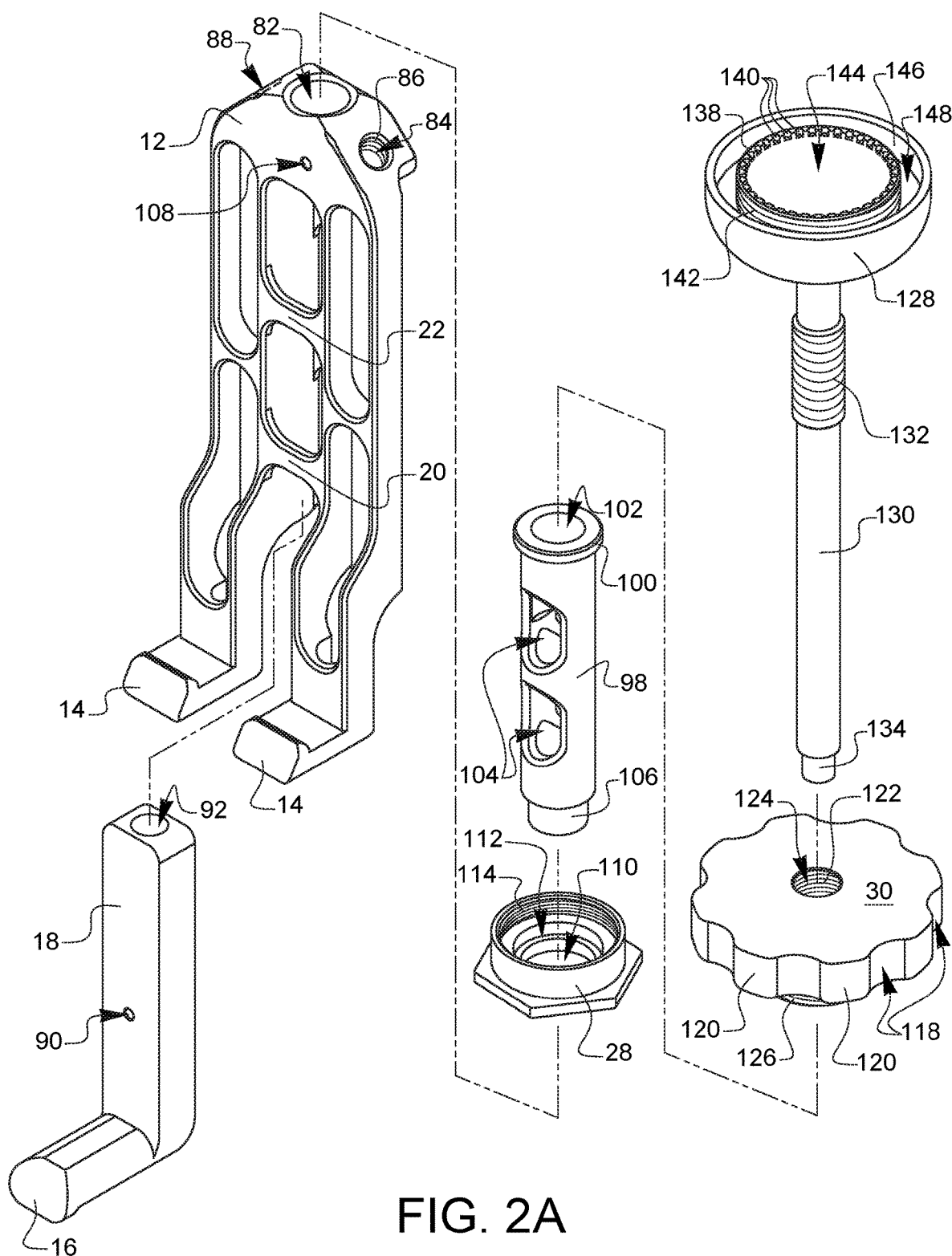
FIGS. 2A-2E are a series of exploded views illustrating the assembly steps of the surgical equipment dock of FIG. 1.

FIGS. 2A-2E are a series of exploded views illustrating the assembly steps of the surgical equipment dock of FIG. 1. FIG. 2A shows the base 12 which defines the lower clamp jaws 14, the lower stop 20, and the upper stop 22. There is also a hole 108 near the top of the base 12 for the insertion of a stop pin 24. The base is configured to slidably receive the upper clamp jaw shaft 18 which defines the upper clamp jaw 16. This upper jaw 16 is movable relative to the lower clamp jaws 14 on the base 12 and can be tightened onto a variety of surgical table rails or fixed to other structures. The upper clamp jaw shaft 18 also has a hole 90 configured to receive a stop pin 24 and a hole 92 configured to receive the shaft step 134 of the inner shaft 130. The base 12 also defines a center arm mount hole 82 and two side arm mounts 84, 88. The two side arm mounts 84, 88 have threads 86 for attaching side arms to the base 12.

Next, a hollow outer shaft 98 is inserted through a hole 110 in the locking nut 28 and fixedly attached to the base 12 by inserting the shaft step 106 portion of the outer shaft 98 first into the center arm mount hole 82 on the base 12. The locking nut 28 is held captive on the outer shaft 98 since the diameter of the step 112 inside the locking nut 28 is sized and configured to mate with and be smaller diameter than the step 100 on the upper end of the outer shaft 98. The shaft step 106 is fitted into center arm mount hole 82 on the base 12. This can be attached by welding, adhesion, or other methods known in the arts. The outer shaft 98 also has several lateral openings 104 configured to enable cleaning and/or sterilization procedures to reach the insides of the central docking arm 26. The central docking arm 26 also has a central hole 102 configured to receive the inner shaft 130. The threads 114 on the locking nut 28 mate with the outer threads 126 on the body lock knob 30 on either side of the step 100 on the outer shaft 98. The inner shaft 130 is then inserted into center hole 124 of inner shaft 130, through the central hole 102 of the outer shaft 98, and into center arm mount hole 82 of base 12 to be fixedly attached to upper clamp jaw shaft 18. The shaft step 134 on the inner shaft 130 mates with the hole 92 of the upper clamp jaw shaft 18. Once the inner shaft 130 is inserted through the outer shaft 98, the hollow outer rod or outer shaft 98 is disposed over the inner shaft 130 or rod and the inner shaft 130 is free to rotate within the outer shaft 98. The body lock knob 30 defines inner threads 122 inside the center hole 124 as well as outer threads 126 on the underside of the body lock knob 30. The body lock knob 30 also defines several recesses 118 and protrusions 120 to form an ergonomic gripping surface for handling the body lock knob 30.

The inner shaft 130 also defines a central ball cup 128 towards the upper portion. The ball cup 128 further defines an outer recess wall 146 and an inner recess wall 138. The outer surface of the inner recess wall 138 has threads 142 and there is a socket recess 148 defined by the space between the outer recess wall 146 and the inner recess wall 138. The threads 142 and socket recess 148 are configured for accepting an attachment nut, which is not shown here, but will be discussed later. The inner recess wall 138 further defines several knurls 140 on the top edge, configured to aid in gripping a large coupler ball 38, shown later, as well as a central ball recess 144. In operation, the upper threads 132 of inner shaft 130 and inner threads 122 on the body lock knob 30 enmesh and when the body lock knob 30 is rotated clockwise, the upper threads 132 drive the inner shaft 130 in a downward direction, thereby moving the upper clamp jaw 16 closer to the lower clamp jaws 14 and closing or tightening the lower clamp jaws 14 and upper clamp jaw 16 together. When the body lock knob 30 is rotated counterclockwise, the upper threads 132 drive the inner shaft 130 in an upward direction, thereby moving the upper clamp jaw 16 further away from the lower clamp jaws 14 and loosening the lower clamp jaws 14 and upper clamp jaw 16 apart from one another. Once the relative positions of the lower clamp jaws 14 and upper clamp jaw 16 is obtained and sufficient clamping force is achieved, the threads 114 on locking nut 28 and the outer threads 126 on body lock knob 30 are tightened to lock the position of the lower clamp jaws 14 and upper clamp jaw 16 in the desired position when clamped to a surgical table rail or other structure. Other embodiments may have alternate tightening mechanisms or have the body lock clamp configured to rotate counterclockwise to tighten and clockwise to loosen.

Figure 2B:
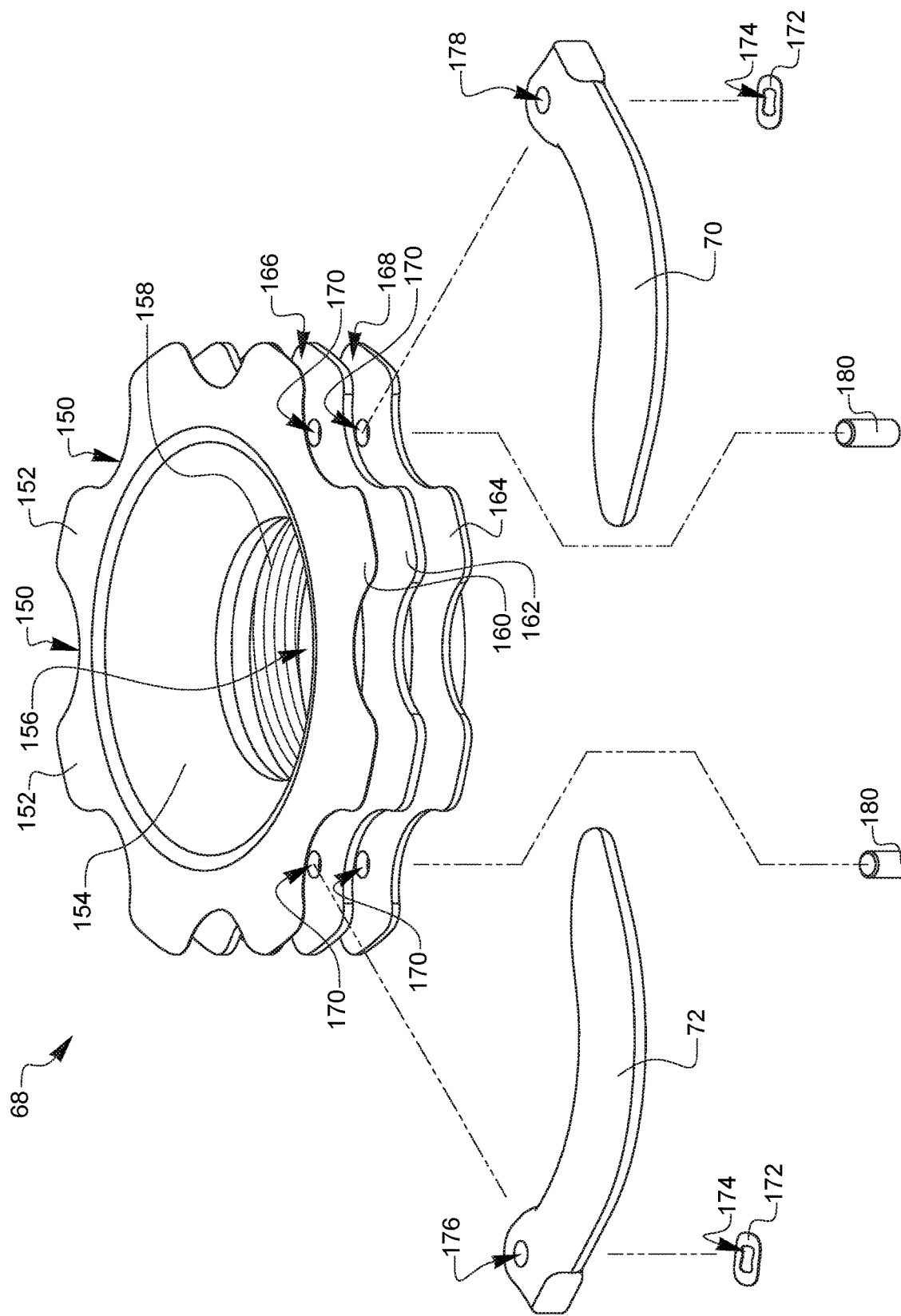

FIG. 2B is an exploded view of a portion of the assembly of the surgical equipment holder dock 10 of FIG. 1, focusing on an attachment nut 68, also known as an attachment nut. The attachment nut 68 has a generally disc-shaped structure. The top layer 160, mid layer 162, and bottom layer 164 are flat, thin segments defined by the attachment nut 68 that extend outward from the center structure of the attachment nut 68. The attachment nut 68, including the top layer 160, mid layer 162, and bottom layer 164 further define several recesses 150 and protrusions 152 encircling the circumference of the attachment nut 68. These recesses 150 and protrusions 152 form an ergonomic gripping feature on the overall form of the attachment nut 68, which may enable or facilitate hand tightening of the attachment nut 68 by providing gripping features. The attachment nut 68 also defines a bevel 154 which permits clearance for any attachments to be positioned at greater angles and with increased clearance. The spacing between the top layer 160, mid layer 162, and bottom layer 164 define an upper slot 166 and a lower slot 168. The mid layer 162 and bottom layer 164 define several holes 170. An upper extendable moment arm 72 and a lower extendable moment arm 70, each having a mounting hole 176, 178 are placed in the upper slot 166 and slot 168, respectively, aligning the hole 176 on the upper extendable moment arm 72 with two of the holes 170 in the attachment nut 68 and aligning the hole 178 on the lower extendable moment arm 70 with two of the holes 170 on the attachment nut 68. A rectangular wave washer 172 having a hole 174 is placed under each of the holes 176, 178 in the respective upper extendable moment arm 72 and lower extendable moment arm 70. Two pins 180 are inserted through the hole 174 of each washer 172, through each hole, 176, 178, through each extendable moment arm 72, 70 while capturing each pin 180 in the corresponding holes 170 of the attachment nut 68. In this embodiment of an attachment nut 68, there are two upper extendable moment arms 72 and two extendable moment arms 70, one of each which are attached on the opposite side of the attachment nut 68 not visible in FIG. 2B. The rectangular washer 172 is shaped and configured to hold the extendable moment arms 70, 72 in place with the overall circumference of the attachment nut 68, but also hold the extendable moment arms 70, 72 extended when desired as required for its functional operation, which will be described later. The rectangular wave washer is not flat and provides a biasing force against the extendable moment arms 70, 72 and the inner portions of the attachment nut 68. While this embodiment of an attachment nut 68 has two upper and two lower extendable moment arms, other embodiments may have fewer, or more, or differently shaped or oriented extendable moment arms. Likewise, alternative shapes and features are possible for other embodiments of the attachment nut 68. Other types of washers or biasing elements may be used to provide a frictional force to hold the extendable moment arms 70, 72 in place, such as triple wave washers, wave washers, spring washers, Belleville washers, disc springs, or combinations thereof.

Figure 2C:
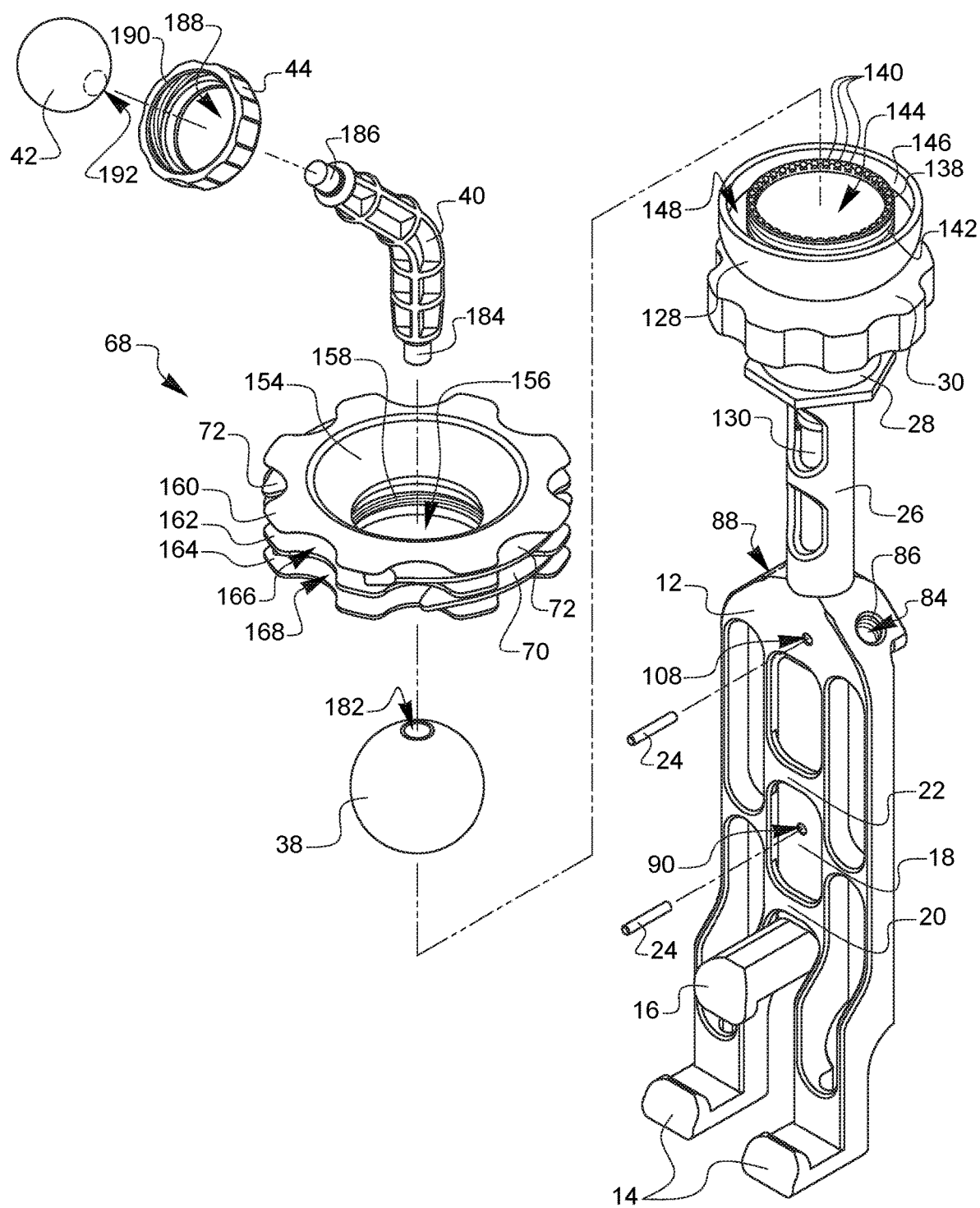
Figure 2D:
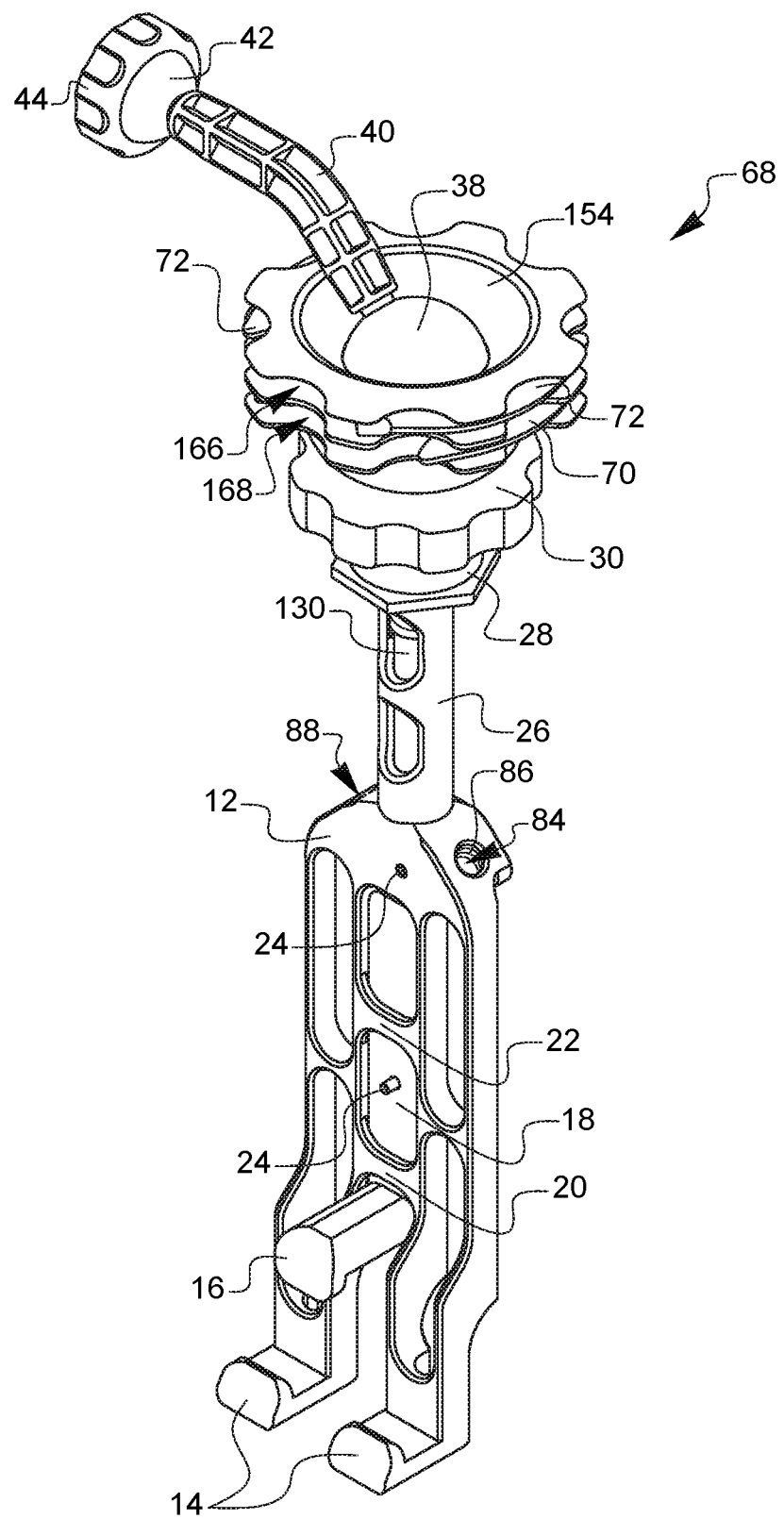

FIG. 2C is an exploded view of a portion of the assembly of the surgical equipment holder dock 10 of FIG. 1, focusing on the combination of the subassemblies illustrated in FIGS. 2A and 2B. Two pins 24 are inserted into holes 90 and 108, respectively, to continue the assembly of the resulting subassembly shown in FIG. 2A. The large coupler ball 38 is placed within the ball recess 144 of the ball cup 128. The coupler rod 40 is passed through the attachment socket recess 156 of the attachment nut 68 and the shaft step 184 of the coupler rod 40 is inserted and fixedly attached to a hole 182 on the large coupler ball 38. A shaft step 186 on the opposite end of the coupler rod 40 is passed through a center hole 188 on the retainer ring 44 and is fixedly attached into a hole 192 on the small coupler ball 42. Once the large coupler ball 38 and the small coupler ball 42 are attached to the coupler rod 40, the attachment nut 68 is attached to the ball cup 128 by engaging the threads 158 with the threads 142 on the ball cup 128 on the inner recess wall 138 of the ball cup 128. Once the threads 158, 142 are engaged, the attachment nut 68 is rotated clockwise to tighten the attachment nut 68 onto the ball cup 128, thereby capturing the large coupler ball 38 between the attachment nut 68 and the ball recess 144 of the ball cup 128. This state of assembly is illustrated in FIG. 2D. When the attachment nut 68 is tightened onto the ball cup 128, the movement of large coupler ball 38 is restricted, and therefore anything attached to the large coupler ball 38, including the coupler rod 40 and any further attachments, are held in place once the attachment nut 68 is tightened on the ball cup 128. The knurls 140 around the top edge of the inner recess wall 138 help provide frictional contact with the large coupler ball 38 to hold the large coupler ball 38 in place. When the attachment nut 68 is loosened from the ball cup 128, the movement of large coupler ball 38 is no longer restricted, and therefore anything attached to the large coupler ball 38, including the coupler rod 40 and any further attachments, are able to move freely in multiple directions. Other embodiments may not include these knurls 140, or teeth to provide frictional forces on the large coupler ball 38. Other embodiments may incorporate textural features on the surface of the coupler ball 38 to enable increased holding forces on the ball.

Figure 2E:
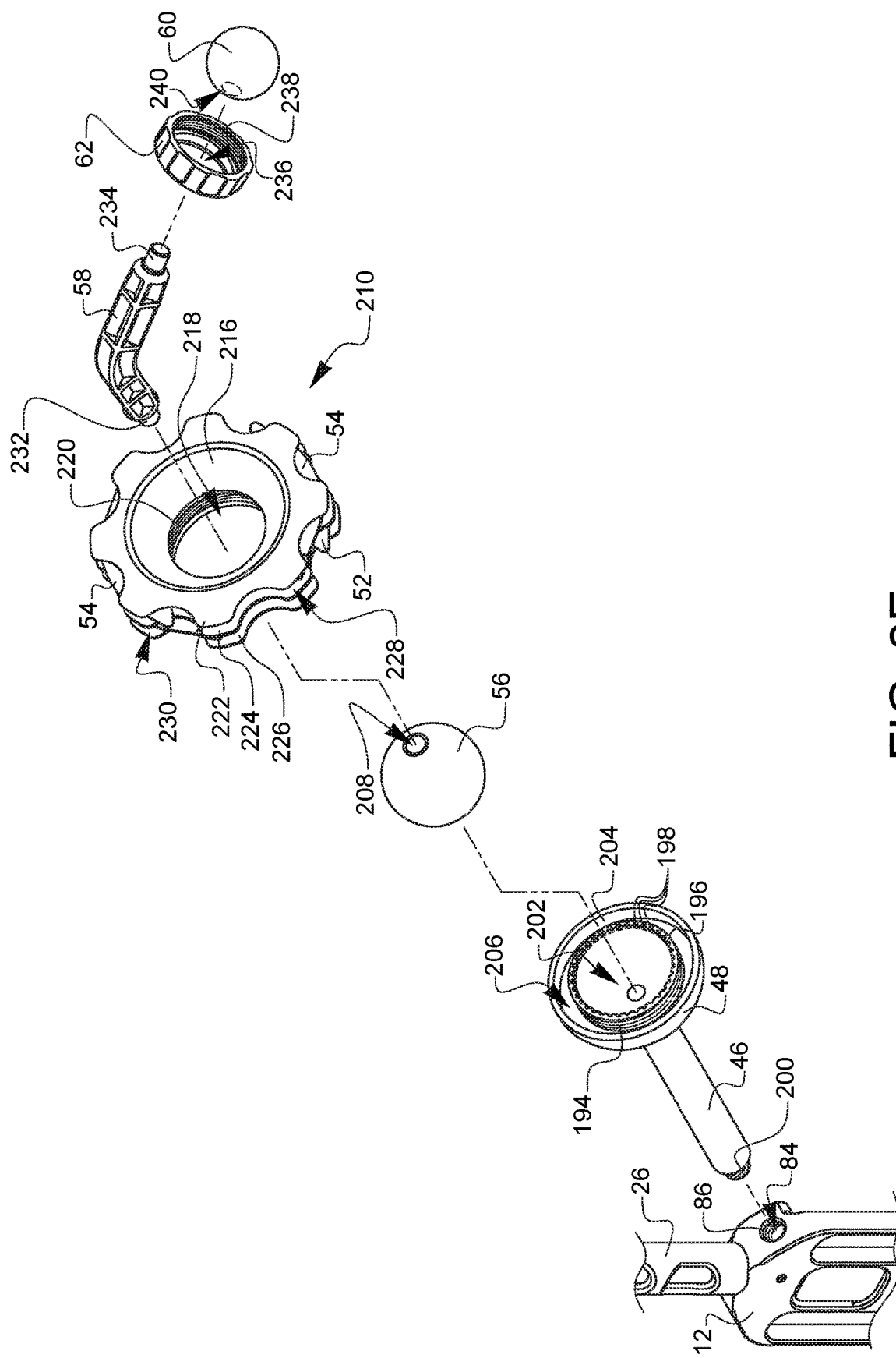

FIG. 2E is an exploded view of a portion of the assembly of the surgical equipment holder dock 10 of FIG. 1, focusing on the assembly of a side arm. On the base 12 is the side arm mount 84 which has threads 86 that correspond to threads 200 on the end of the shaft of the first side docking arm 46. The first side docking arm 46 is similar in structure to the central docking arm 26, discussed previously, but is simpler in nature in terms of some of its structural features. The first side docking arm 46 has a ball cup 48 towards the upper portion. The ball cup 48 further defines an outer recess wall 204 and an inner recess wall 196. The outer surface of the inner recess wall 196 has threads 194 and there is a socket recess 206 defined by the space between the outer recess wall 204 and the inner recess wall 196. The threads 194 and socket recess 206 are configured for accepting attachment nut 210. The inner recess wall 196 further defines several knurls 198 on the top edge of the inner recess wall 196, configured to aid in gripping a large coupler ball 56, as well as a central ball recess 202. The large coupler ball 56 is placed within the ball recess 202 of the ball cup 48. The coupler rod 58 is passed through the attachment socket recess 218 of the attachment socket 210 and the shaft step 232 of the coupler rod 58 is inserted and fixedly attached into a hole 208 on the large coupler ball 56. A shaft step 234 on the opposite end of the coupler rod 58 is passed through a center hole 236 on the retainer ring 62 and is fixedly attached into a hole 240 on the small coupler ball 60. Once the large coupler ball 56 and the small coupler ball 60 are attached to the coupler rod 58, the attachment socket 210 is attached to the ball cup 48 by engaging the threads 194 on the ball cup 48 with the threads 220, not visible in this view, but similar to the one discussed previously in regard to FIG. 2C on the ball cup 48 on the inner recess wall 196 of the ball cup 48. Once the threads 194 are engaged, the attachment socket 210 is rotated clockwise to tighten the attachment socket 210 onto the ball cup 48, thereby capturing the large coupler ball 56 between the attachment socket 210 and the ball recess 202 of the ball cup 48. When the attachment socket 210 is tightened onto the ball cup 48, the movement of large coupler ball 56 is restricted, and therefore anything attached to the large coupler ball 56, including the coupler rod 58 and any further attachments, are held in place once the attachment socket 210 is tightened on the ball cup 48. The knurls 198 around the top edge of the inner recess wall 196 help provide frictional contact with the large coupler ball 56 to hold the large coupler ball 56 in place. When the attachment socket 210 is loosened from the ball cup 48, the movement of large coupler ball 56 is no longer restricted, and therefore anything attached to the large coupler ball 56 including the coupler rod 58 and any further attachments, are able to move freely in multiple directions.

The attachment socket 210, as previously described, has a generally disc-shaped structure. The top layer 222, mid layer 224, and bottom layer 226 are flat, thin segments defined by the attachment socket 210 that extend outward from the center structure of the attachment socket 210. The attachment socket 210, including the top layer 222, mid layer 224, and bottom layer 226 further define several recesses and protrusions encircling the circumference of the attachment socket 210. These recesses and protrusions form an ergonomic gripping feature on the overall form of the attachment socket 210, which may enable or facilitate hand tightening of the attachment socket 210 by providing gripping features. The spacing between the top layer 222, mid layer 224, and bottom layer 226 define an upper slot 228 and a lower slot 230. The attachment socket 210 also has two upper extendable moment arms 54 and two lower extendable moment arms 52, which are attached to the attachment socket 210 in a similar manner as previously described in regard to the attachment nut 68 in FIG. 2B. While this embodiment of an attachment nut 68 has two upper and two lower extendable moment arms, other embodiments may have fewer, or more, or differently shaped or oriented extendable moment arms. Likewise, alternative shapes and features are possible for other embodiments of the attachment nut 68. While not shown in these views, the assembly of the second docking arm is similar to the assembly of the first side docking arm attachment shown in FIG. 2E.

Figure 3A:
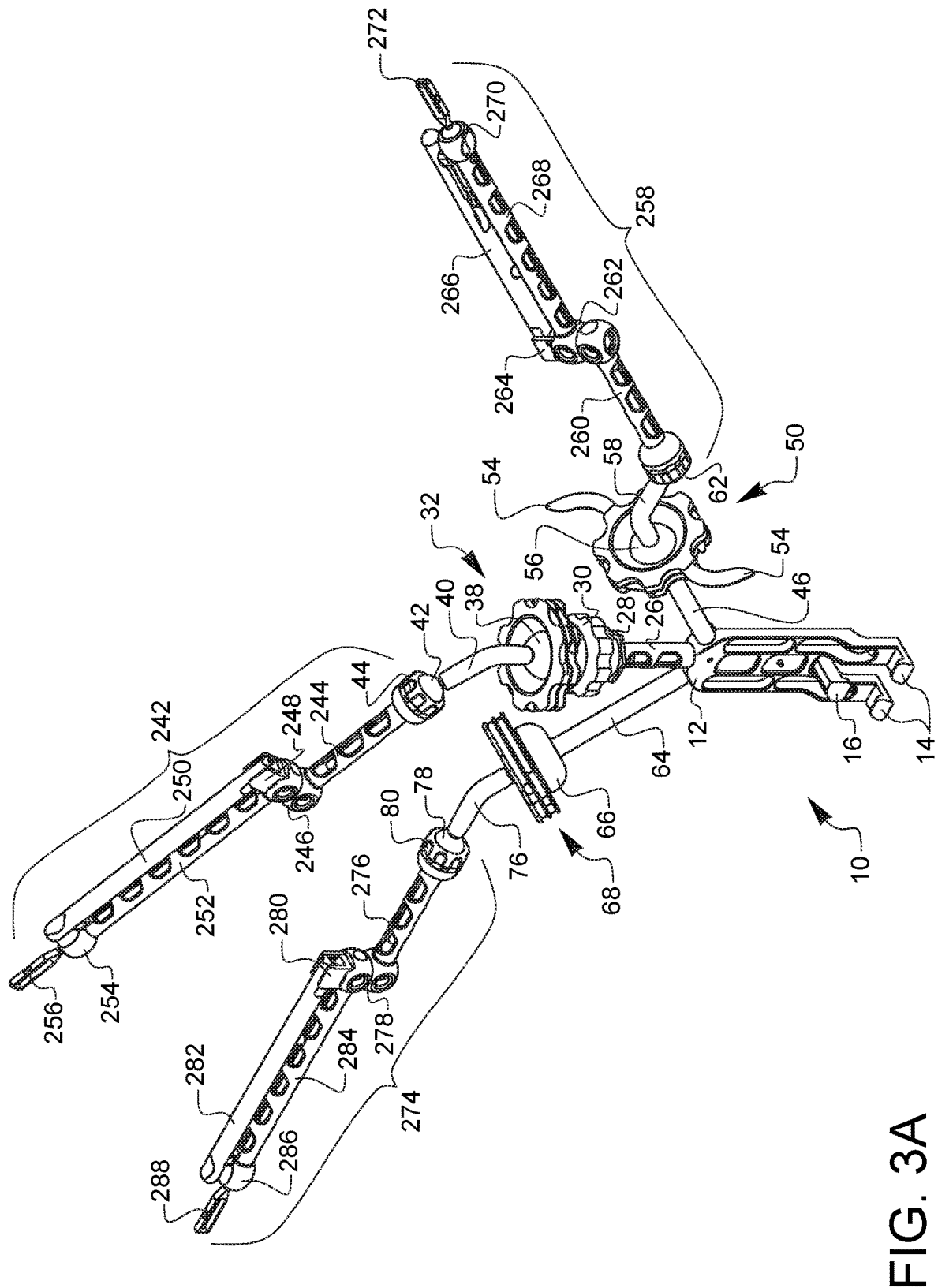
FIGS. 3A and 3B are top-right-front perspective views of the surgical equipment dock holder of FIG. 1 with two additional side arms in addition to a central docking arm and three surgical equipment holders mounted on each arm.
Figure 3B:
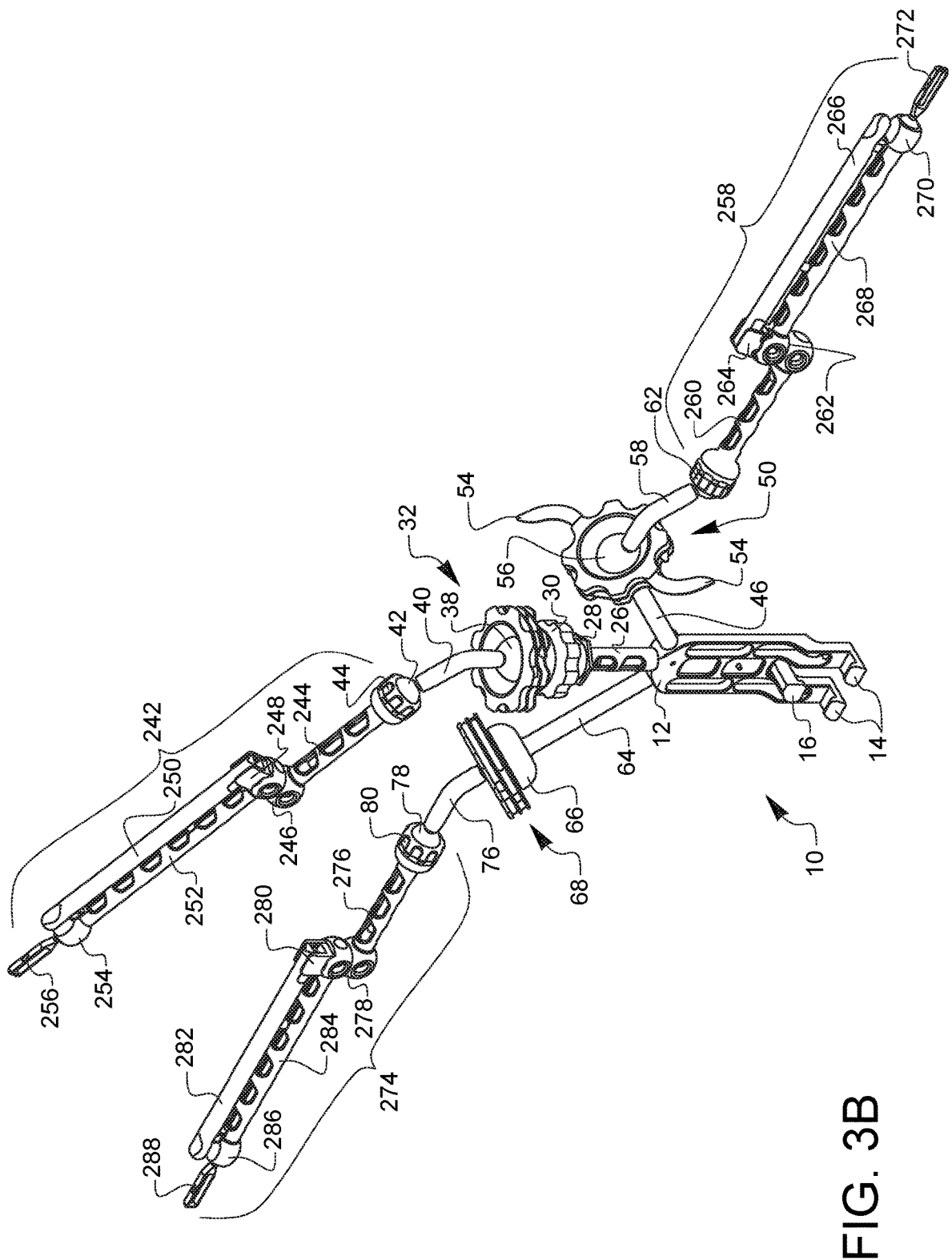

FIGS. 3A and 3B are top-right-front perspective views of the surgical equipment dock holder of FIG. 1 with two side arms in addition to a central docking arm and three surgical equipment holders mounted on each arm. The surgical equipment holder dock 10 comprises a base 12 which defines a lower clamp jaws 14 and has an upper clamp jaw 16 which is movable and slidably engaged within the base 12. A central docking arm 26 is attached at the top of the base 12. The central docking arm 26 has a locking nut 28 and a body lock knob 30 and attachment nut 32 connected to the central docking arm 26 as described previously in regard to FIG. 1. Releasably held between the body lock knob 30 and the attachment nut 32 is the large coupler ball 38 connected to the coupler rod 40. A small coupler ball 42 and retainer ring 44 attached at the opposite end of the coupler rod 40 are fastened to a central surgical equipment holder arm assembly 242. The central surgical equipment holder arm assembly 242 has a first arm 244 attached to the retainer ring 44, a locking joint 246 which joins the second arm 252 to the first arm 244. A lever block 248 having an operating lever 250 is located at the top of the locking joint 246. The second arm 252 also has an end joint 254 which includes an end effector 256. The end effector 256 is an attachment point for attaching any number of surgical equipment to the end of the central surgical equipment holder arm assembly 242. In this configuration, a piece of surgical equipment, would be easily repositionable by adjusting the central surgical equipment holder arm assembly 242. The operating lever 250 is configured to lock and unlock the joints of the central surgical equipment holder arm assembly 242 at the small coupler ball 42, locking joint 246 and end joint 254, allowing the joint to move freely when unlocked, and holding the small coupler ball 42, locking joint 246, and end joint 254 in a locked position, therefore keeping the relative positions of the first arm 244, second arm 252, and end effector 256 in position.

The base 12 of the surgical equipment holder dock 10 also includes a first side docking arm 46 connected to a side arm attachment nut 50, holding another coupler rod 58 in position. This coupler rod 58 also has a large coupler ball 56 held between the ball cup 48 connected to the first side docking arm 46 and the attachment nut 50. The upper extendable moment arms 54 are shown extended, indicating that that attachment nut 50 is being tightened. This will be further described later. A small coupler ball 42 (not visible here) and retainer ring 62 attached at the opposite end of the coupler rod 40 are fastened to a first side surgical equipment holder arm assembly 258. The first side surgical equipment holder arm assembly 258 has a first arm 260 attached to the retainer ring 62, a locking joint 262 which joins the second arm 268 to the first arm 260. A lever block 264 having an operating lever 266 is located at the top of the locking joint 262. The second arm 268 also has an end joint 270 which includes an end effector 272. The end effector 272 is an attachment point for attaching any number of surgical equipment to the end of the first side surgical equipment holder arm assembly 258. In this configuration, a piece of surgical equipment, would be easily repositionable by adjusting the first side surgical equipment holder arm assembly 258. The operating lever 266 is configured to lock and unlock the joints of the first side surgical equipment holder arm assembly 258 at the small coupler ball 60, locking joint 262 and end joint 270, allowing the joint to move freely when unlocked, and holding the small coupler ball 42, locking joint 246, and end joint 254 in a locked position, therefore keeping the relative positions of the first arm 260, second arm 268, and end effector 272 in position.

The base 12 of the surgical equipment holder dock 10 also includes a second side docking arm 64 connected to a side arm attachment nut 68, holding another coupler rod 76 in position. This coupler rod 76 also has a large coupler ball, not visible here, held between the ball cup 66 connected to the first side docking arm 64 and the attachment nut 68. A small coupler ball 78 and retainer ring 80 attached at the opposite end of the coupler rod 76 are fastened to a second side surgical equipment holder arm assembly 274. The second side surgical equipment holder arm assembly 274 has a first arm 276 attached to the retainer ring 80, a locking joint 278 which joins the second arm 284 to the first arm 276. A lever block 280 having an operating lever 282 is located at the top of the locking joint 278. The second arm 284 also has an end joint 286 which includes an end effector 288. The end effector 288 is an attachment point for attaching any number of surgical equipment to the end of the second side surgical equipment holder arm assembly 274. In this configuration, a piece of surgical equipment, would be easily repositionable by adjusting the second side surgical equipment holder arm assembly 274. The operating lever 282 is configured to lock and unlock the joints of the second side surgical equipment holder arm assembly 274 at the small coupler ball 78, locking joint 278 and end joint 286, allowing the joint to move freely when unlocked, and holding the positions of the small coupler ball 78, locking joint 278, and end joint 286 in a locked position, therefore keeping the relative positions of the first arm 276, second arm 284, and end effector 288 in position. FIG. 3B is a top-right-front perspective view of the surgical equipment dock holder arrangement shown in FIG. 3A, with the first side surgical equipment holder arm assembly 258 shown in a lowered position relative to the position illustrated in FIG. 3A.

FIGS. 4A, 4B, 4C, 4D and 4E are a series of top perspective views of a torque enhancing apparatus of the surgical equipment dock holder of FIG. 1 illustrating two pair of moment arms retracted, a pair of lower moment arms extended, the pair of lower moment arms in use for loosening, a pair of upper moment arms extended, and the pair of upper moment arms in use for tightening, respectively. The other components and elements of the surgical equipment holder dock 10 are removed for the purposes of showing the socket operation more clearly.

Figure 4A:
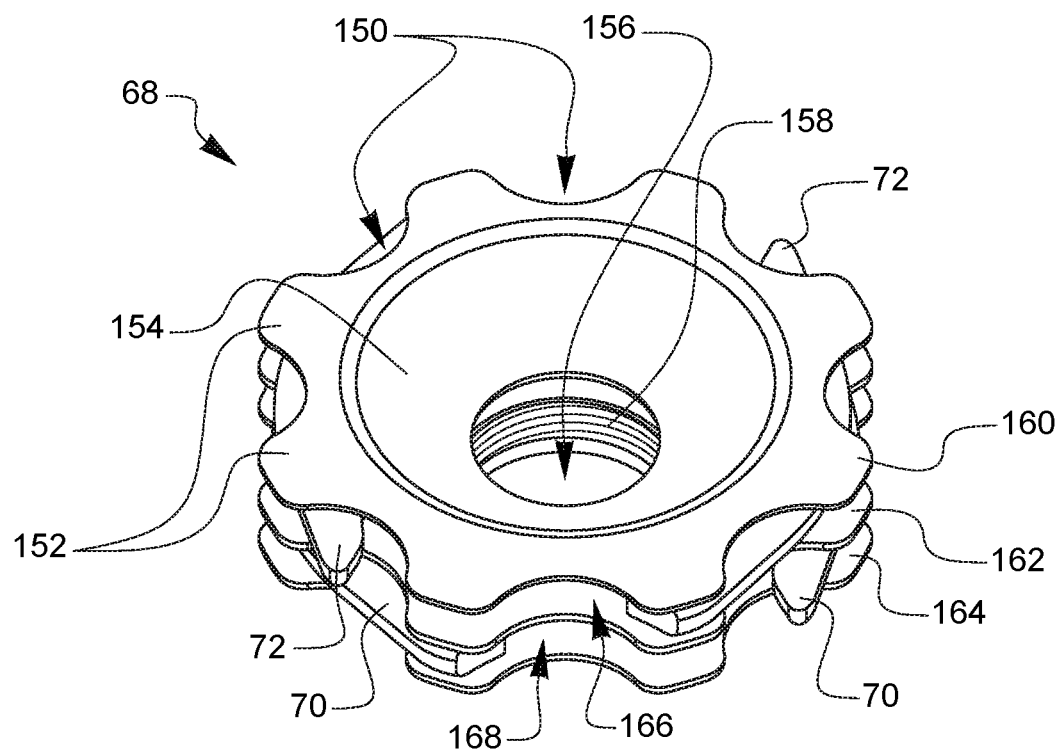
FIGS. 4A, 4B, 4C, 4D and 4E are a series of top perspective views of a torque enhancing apparatus of the surgical equipment dock holder of FIG. 1 illustrating two pair of moment arms retracted, a pair of lower moment arms extended, the pair of lower moment arms in use for loosening, and a pair of upper moment arms extended, and the pair of upper moment arms in use for tightening, respectively.

FIG. 4A is a top perspective view of a torque enhancing apparatus or attachment socket. This attachment socket, its features, and the assembly thereof has been described in regard to FIG. 2B. In FIG. 4A, the attachment socket is illustrated with both upper extendable moment arms 72 and both lower extendable moment arms 70 in a retracted or tucked in position. When retracted, the position of the moment arms 70, 72 closely follows the circumference of the disc shape of the attachment nut 68.

Figure 4B:
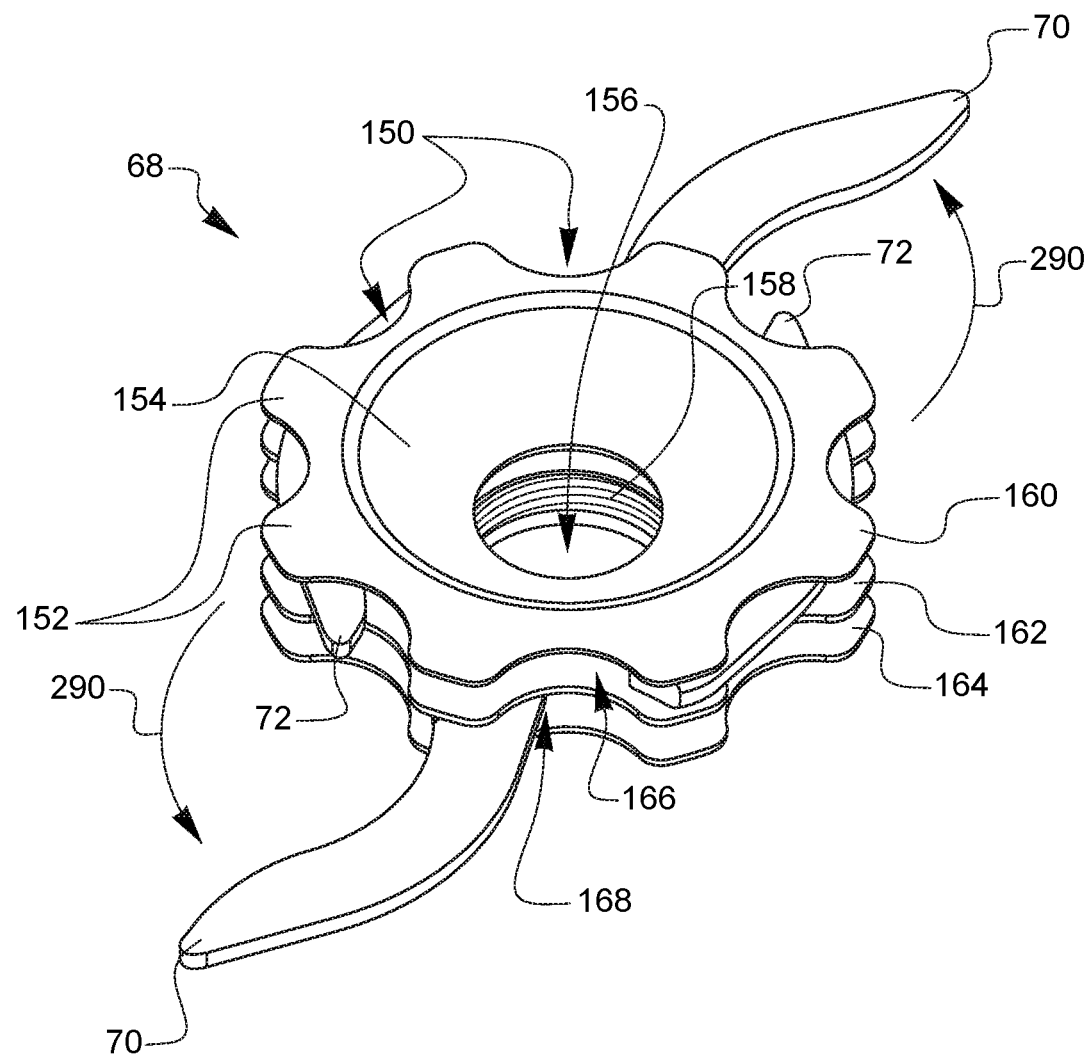

FIG. 4B is a top perspective view of a torque enhancing apparatus or attachment socket with a pair of lower moment arms extended. Each of the four extendable moment arms 70, 72 have a biasing restraint, in this embodiment the rectangular washer 172 as described in regard to FIG. 4B, configured to restrain each extendable moment arm 70 in either the retracted or extended position once moved to said positions. A sufficient force must be applied to defeat the biasing restraint in order to extend each of the lower moment arms 70 in an outward direction 290.

Figure 4C:
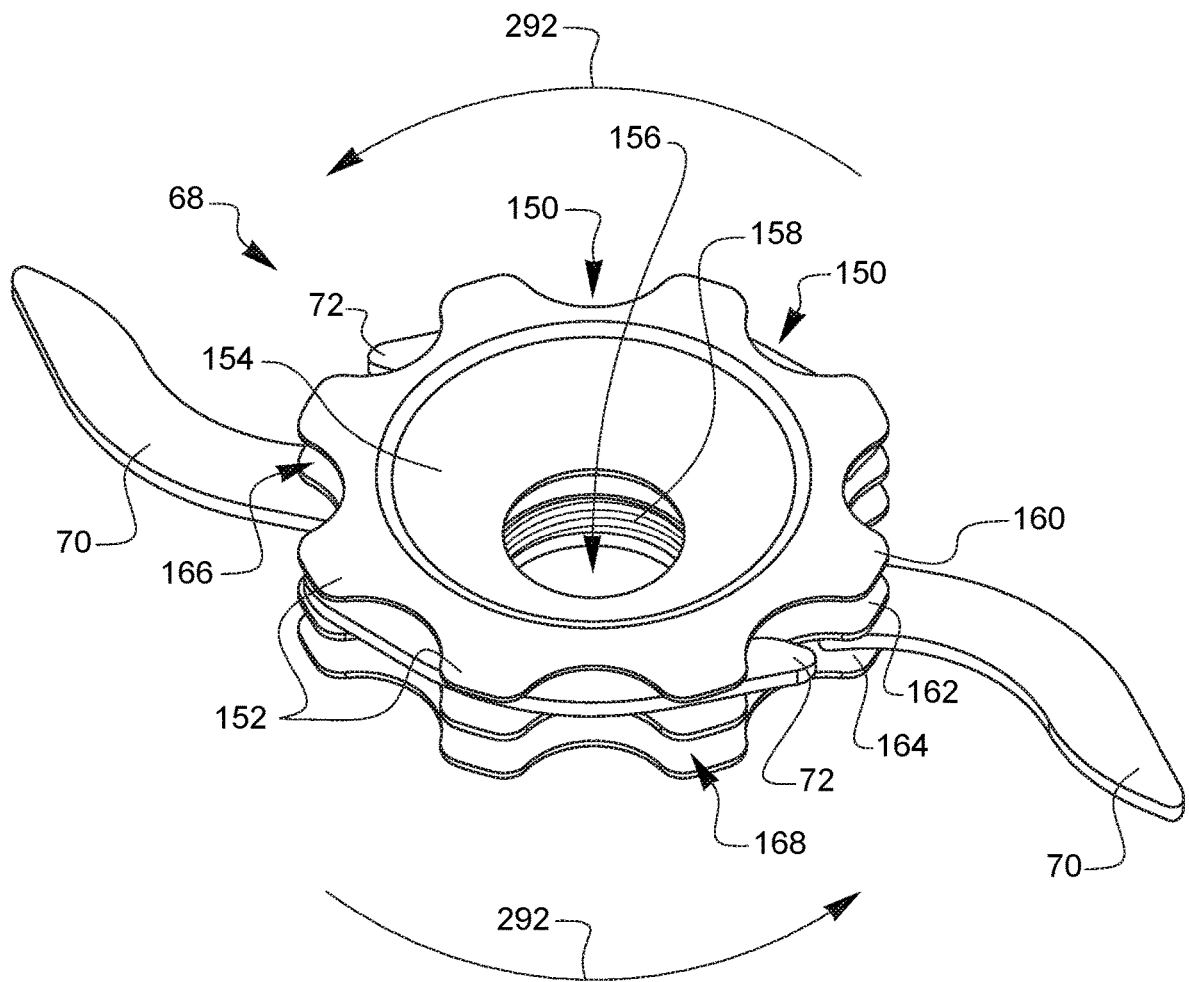

FIG. 4C is a top perspective view of a torque enhancing apparatus or attachment socket with a pair of lower moment arms in use for loosening. FIG. 4C shows the attachment socket of FIG. 4A with the two lower extendable moment arms 70 extended and the two upper extendable moment arms 72 retracted, the two lower extendable moment arms 70 providing a mechanical advantage for loosening the attachment nut 68 relative to the ball cup 66 of the second side docking arm 64. The attachment nut 68 may now be rotated in a counterclockwise direction 292 in order to loosen the large coupler ball 74 of the bent coupler rod 76 between the attachment nut 68 and the ball cup 66 of the second side docking arm 64 with reduced force as compared to when the lower extendable moment arms 70 are retracted, which provides a mechanical advantage.

Figure 4D:
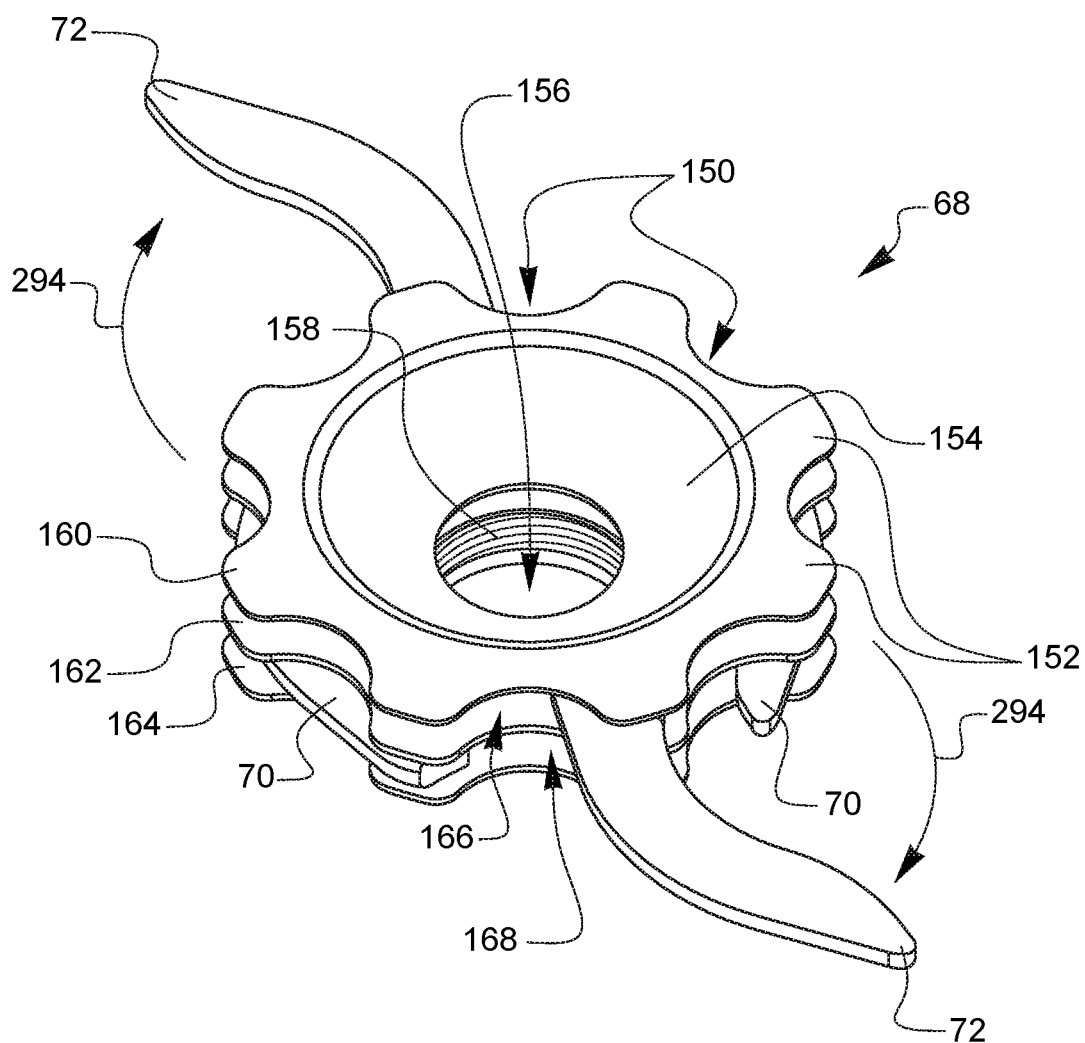

FIG. 4D is a top perspective view of a torque enhancing apparatus or attachment socket with a pair of upper moment arms extended. Each of the four extendable moment arms 70, 72 have a biasing restraint, in this embodiment, the rectangular washer 172 as described in regard to FIG. 4B, configured to restrain each upper extendable moment arm 72 in either the retracted or extended position once moved to said position. A sufficient force must be applied to defeat the biasing restraint in order to extend each of the lower moment arms 72 in an outward direction 294.

Figure 4E:
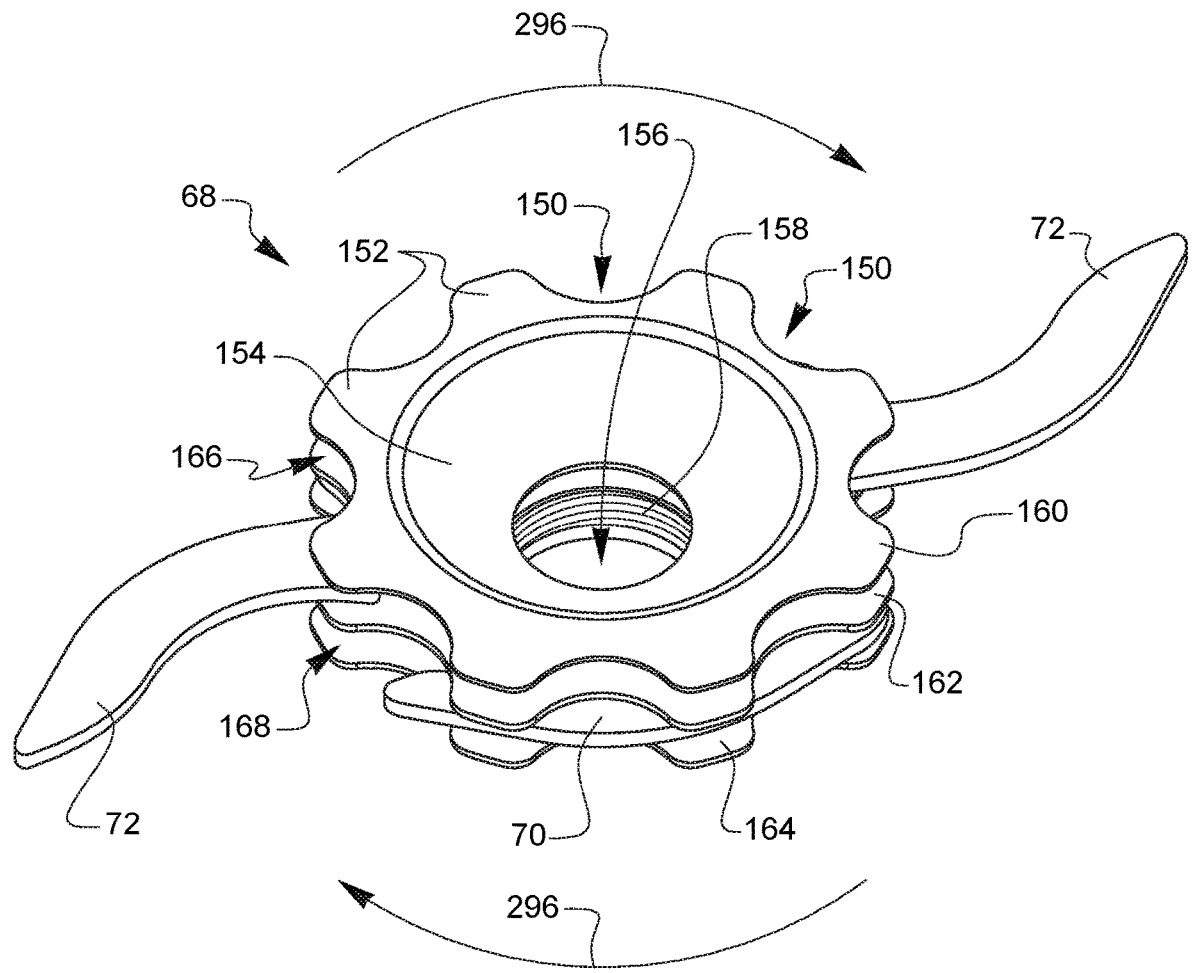

FIG. 4E is a top perspective view of a torque enhancing apparatus or attachment socket with a pair of upper moment arms in use for tightening torque enhancing apparatus. FIG. 4E shows the attachment socket of FIG. 4A with the two upper extendable moment arms 72 extended and the two lower extendable moment arms 70 retracted, the two upper extendable moment arms 72 providing a mechanical advantage for tightening the attachment nut 68 relative to the ball cup 66 of the second side docking arm 64. The attachment nut 68 may now be rotated in a clockwise direction 296 in order to tighten the large coupler ball 74 of the bent coupler rod 76 between the attachment nut 68 and the ball cup 66 of the second side docking arm 64 with reduced force as compared to when the upper extendable moment arms 72 are retracted, which provides a mechanical advantage. Alternate embodiments of attachment sockets or torque enhancing apparatus may have other arrangements and orientations of extendable moment arms that may or may not overlap, may slide back and forth from a retracted to extended position, may be detachable, or combinations thereof. Alternate embodiments of attachment sockets or torque enhancing apparatus may be directionally oriented such that a clockwise rotation is loosening, and counterclockwise rotation is tightening.

Figure 5:
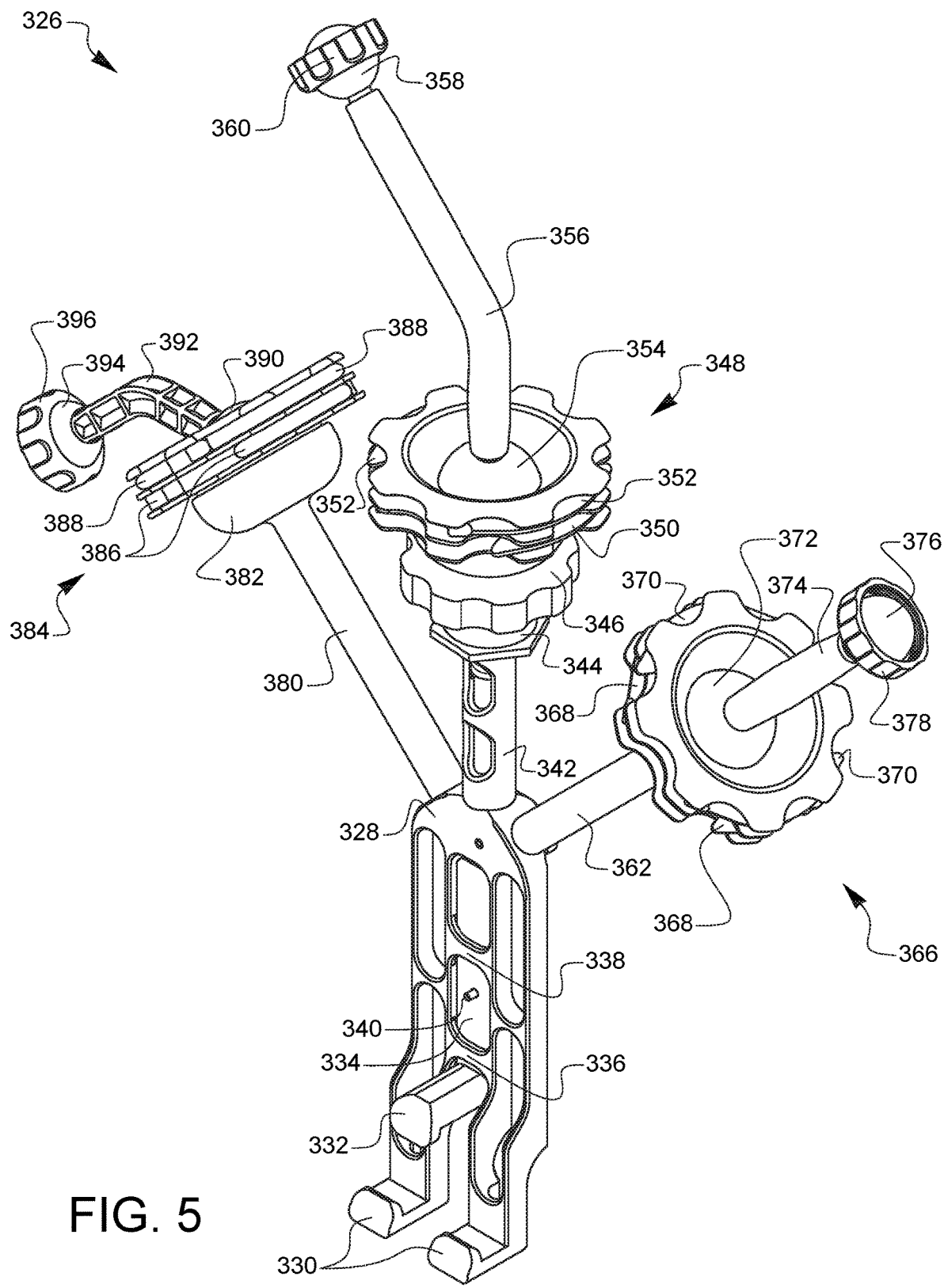
FIG. 5 is a top-right-front perspective view of another embodiment of a surgical equipment holder dock.

FIG. 5 is a top-right-front perspective view of one embodiment of a surgical equipment holder dock. This embodiment of a surgical equipment holder dock 326 includes a base 328 which defines a pair of lower clamp jaws 330, a lower stop 336, and an upper stop 338. Internally movable within the base 328 of the surgical equipment holder dock 326 is an upper clamp jaw 332 connected to an upper clamp jaw shaft 334. The upper clamp jaw shaft 334 includes a stop pin 340 which is located on the upper clamp jaw shaft 334 such that the pin 340 is located between the lower stop 336 and the upper stop 338 and is configured to limit the vertical travel of the upper clamp jaw shaft 334 and therefore the relative position of the upper clamp jaw 332 in relation to the lower clamp jaws 330. The base 328 is configured to clamp the surgical equipment holder dock 326 to a surgical table rail. Attached to the upper portion of the base 328 is a central docking arm 342. This central docking arm 342 has a locking nut 344 attached to the top of the central docking arm 342. Above the locking nut 344 is a body lock knob 346, which is connected to the upper clamp jaw shaft 334 via an inner shaft, which is not explicitly shown in this view, but will be discussed later. Above the body lock knob 346 is a socket (not visible in this view). A central attachment nut 348 is coupled to the socket. The attachment nut 348 includes two lower extendable moment arms 350 and two upper extendable moment arms 352. A large coupler ball 354 is held between the socket attached to the central docking arm 342 and the attachment nut 348. A smooth, bent longer coupler rod 356 is attached on one end to the large coupler ball 354 and attached to a small coupler ball 358 on the opposite end. Over the small coupler ball 358, a retainer ring 360 is connected, which will later serve as a mounting point for a surgical equipment holder (not shown in this view). In addition to the central docking arm 342, the surgical equipment holder dock 326 also has a first side docking arm 362 and a second side docking arm 380 attached to the base 328, each angled at an approximate angle of 45 degrees relative to the central docking arm 342. While a 45-degree angle is shown in this embodiments, other embodiments may have other angles of the side arm as compared to the central docking arm 342. The first side docking arm 362 defines a first side coupling ball cup 364 (not visible in this view) which is configured to combine with a first side attachment nut 366 having two lower extendable moment arms 368 and two upper extendable moment arm 370. A large coupler ball 372 is held between the coupling ball cup 364 and the attachment nut 366. A straight, smooth coupler rod 374 is attached on one end to the large coupler ball 372 and attached to a small coupler ball 376 on the opposite end. Over the small coupler ball 376, a retainer ring 378 is connected, which will later serve as a mounting point for a surgical equipment holder (not shown in this view). The second side docking arm 380 also defines a second side coupling ball cup 382 which is configured to combine with a second side attachment nut 384 having two lower extendable moment arms 386 and two upper extendable moment arms 388. A large coupler ball 390 is held between the coupling ball cup 382 and the attachment nut 384. A bent coupler rod 392 is attached on one end to the large coupler ball 390 and attached to a small coupler ball 394 on the opposite end of the coupler rod 392. Over the small coupler ball 394, a retainer ring 396 is connected, which will later serve as a mounting point for a surgical equipment holder (not shown in this view). The position of each of the coupler rods 356, 374, 392 can be positioned and locked by first loosening one of the attachment nuts 348, 366, 384, placing the position of the coupler rod 356, 374, 392 as desired, and therefore any attached fixturing or devices, such as surgical equipment holders. Next, the attachment nut 348, 366, 384 is tightened, thereby locking the coupler rod 356, 374, 392 into the desired position by clamping the large coupler ball 354, 372, 390 between the attachment nut 348, 366, 384 and each ball cup 364, 382.

Figure 6:
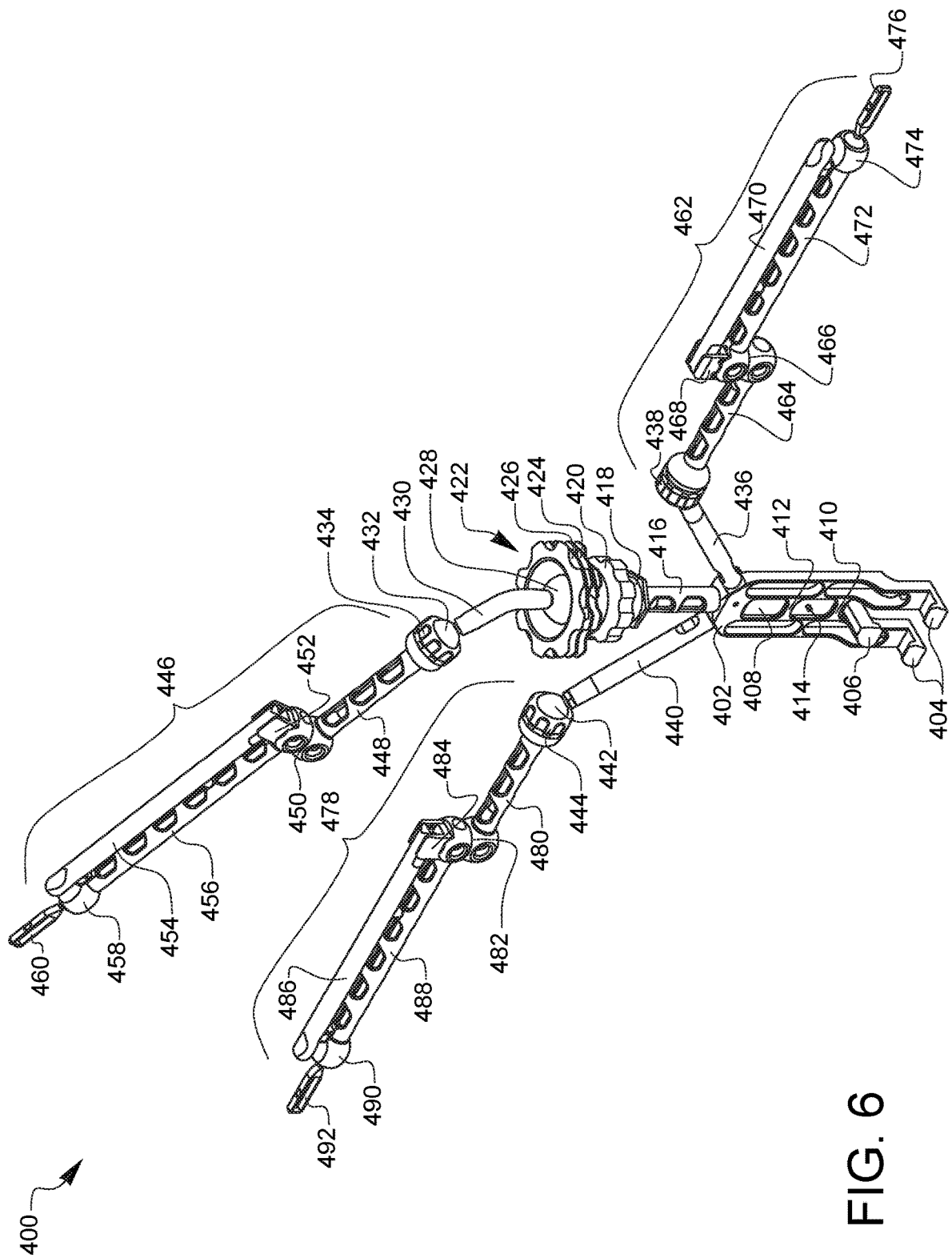
FIG. 6 is a top-right-front perspective view of another embodiment of a surgical equipment holder dock.

FIG. 6 is a top-right-front perspective view of another embodiment of a surgical equipment holder dock. This embodiment of a surgical equipment holder dock 400 includes a base 402 which defines a pair of lower clamp jaws 404, a lower stop 410, and an upper stop 412. Internally movable within the base 402 of the surgical equipment holder dock 400 is an upper clamp jaw 406 connected to an upper clamp jaw shaft 408. The upper clamp jaw shaft 408 includes a stop pin 414 which is located on the upper clamp jaw shaft 408 such that the pin 414 is located between the lower stop 410 and the upper stop 412 and is configured to limit the vertical travel of the upper clamp jaw shaft 408 and therefore the relative position of the upper clamp jaw 406 in relation to the lower clamp jaws 404. Other embodiments may or may not include stop pins and may limit travel of the movable portion of the clamp jaws by means known to those skilled in the arts. Other embodiments may have a movable lower clamp jaws or movable lower and upper clamp jaws. The base 402 is configured to clamp the surgical equipment holder dock 400 to a surgical table rail. Attached to the upper portion of the base 402 is a central docking arm 416. This central docking arm 416 has a locking nut 418 attached to the top of the central docking arm 416. Above the locking nut 418 is a body lock knob 420, which is connected to the upper clamp jaw shaft 408 via an inner shaft, which is not explicitly shown in this view, but will be discussed later. Above the body lock knob 420 is a socket not shown in this view but has been described previously in regard to other embodiments. A central attachment nut 422 is coupled to the socket. The attachment nut 422 includes two lower extendable moment arms 424 and two upper extendable moment arms 426. A large coupler ball 428 is held between the socket attached to the central docking arm 416 and the attachment nut 422. A bent coupler rod 430 is attached on one end to the large coupler ball 428 and attached to a small coupler ball 432 on the opposite end. Over the small coupler ball 432, a retainer ring 434 is connected, which will later serve as a mounting point for a surgical equipment holder. A small coupler ball 432 and retainer ring 434 attached at the opposite end of the coupler rod 430 are fastened to a central surgical equipment holder arm assembly 446. The central surgical equipment holder arm assembly 446 has a first arm 448 attached to the retainer ring 434, a locking joint 450 which joins a second arm 456 to the first arm 448. A lever block 452 having an operating lever 454 is located at the top of the locking joint 450. The second arm 456 also has an end joint 458 which includes an end effector 460. The end effector 460 is an attachment point for attaching any number of surgical equipment to the end of the central surgical equipment holder arm assembly 446. In this configuration, a piece of surgical equipment, would be easily repositionable by adjusting the central surgical equipment holder arm assembly 446. The operating lever 454 is configured to lock and unlock the joints of the central surgical equipment holder arm assembly 446 at small coupler ball 432, locking joint 450 and end joint 458, allowing the joint to move freely when unlocked, and holding the small coupler ball 432, locking joint 450, and end joint 458 in a locked position, therefore keeping the relative positions of the first arm 448, second arm 456, and end effector 460 in a fixed position.

In addition to the central docking arm 416, the surgical equipment holder dock 400 also has a first side docking arm 436 and a second side docking arm 440 attached to the base 402, each angled at an approximate angle of 45-degrees relative to the central docking arm 416. While a 45-degree angle is shown in this embodiments, other embodiments may have other angles of the side arm as compared to the central docking arm 416. A small coupler ball (not visible here) and retainer ring 438 attached at the opposite end of the first side docking arm 436 are fastened to a central surgical equipment holder arm assembly 462. The central surgical equipment holder arm assembly 462 has a first arm 464 attached to the retainer ring 438, a locking joint 466 which joins the second arm 472 to the first arm 464. A lever block 468 having an operating lever 470 is located at the top of the locking joint 466. The second arm 472 also has an end joint 474 which includes an end effector 476. The end effector 476 is an attachment point for attaching any number of surgical equipment to the end of the central surgical equipment holder arm assembly 462. In this configuration, a piece of surgical equipment, would be easily repositionable by adjusting the central surgical equipment holder arm assembly 462. The operating lever 470 is configured to lock and unlock the joints of the central surgical equipment holder arm assembly 462 at the small coupler ball, locking joint 466 and end joint 474, allowing the joint to move freely when unlocked, and holding the small coupler ball, locking joint 466, and end joint 474 in a locked position, therefore keeping the relative positions of the first arm 464, second arm 472, and end effector 476 in a fixed position.

A small coupler ball 442 and retainer ring 444 attached at the opposite end of the second side docking arm 440 are fastened to a second side surgical equipment holder arm assembly 478. The second side surgical equipment holder arm assembly 478 has a first arm 480 attached to the retainer ring 444, a locking joint 482 which joins the second arm 488 to the first arm 480. A lever block 484 having an operating lever 486 is located at the top of the locking joint 482. The second arm 488 also has an end joint 490 which includes an end effector 492. The end effector 492 is an attachment point for attaching any number of surgical equipment to the end of the second side surgical equipment holder arm assembly 478. In this configuration, a piece of surgical equipment, would be easily repositionable by adjusting the second side surgical equipment holder arm assembly 478. The operating lever 486 is configured to lock and unlock the joints of the second side surgical equipment holder arm assembly 478 at the small coupler ball 442, locking joint 482 and end joint 490, allowing the joint to move freely when unlocked, and holding the positions of the small coupler ball 442, locking joint 482, and end joint 490 in a locked position, therefore keeping the relative positions of the first arm 480, second arm 488, and end effector 492 in a fixed position.

Figure 7:
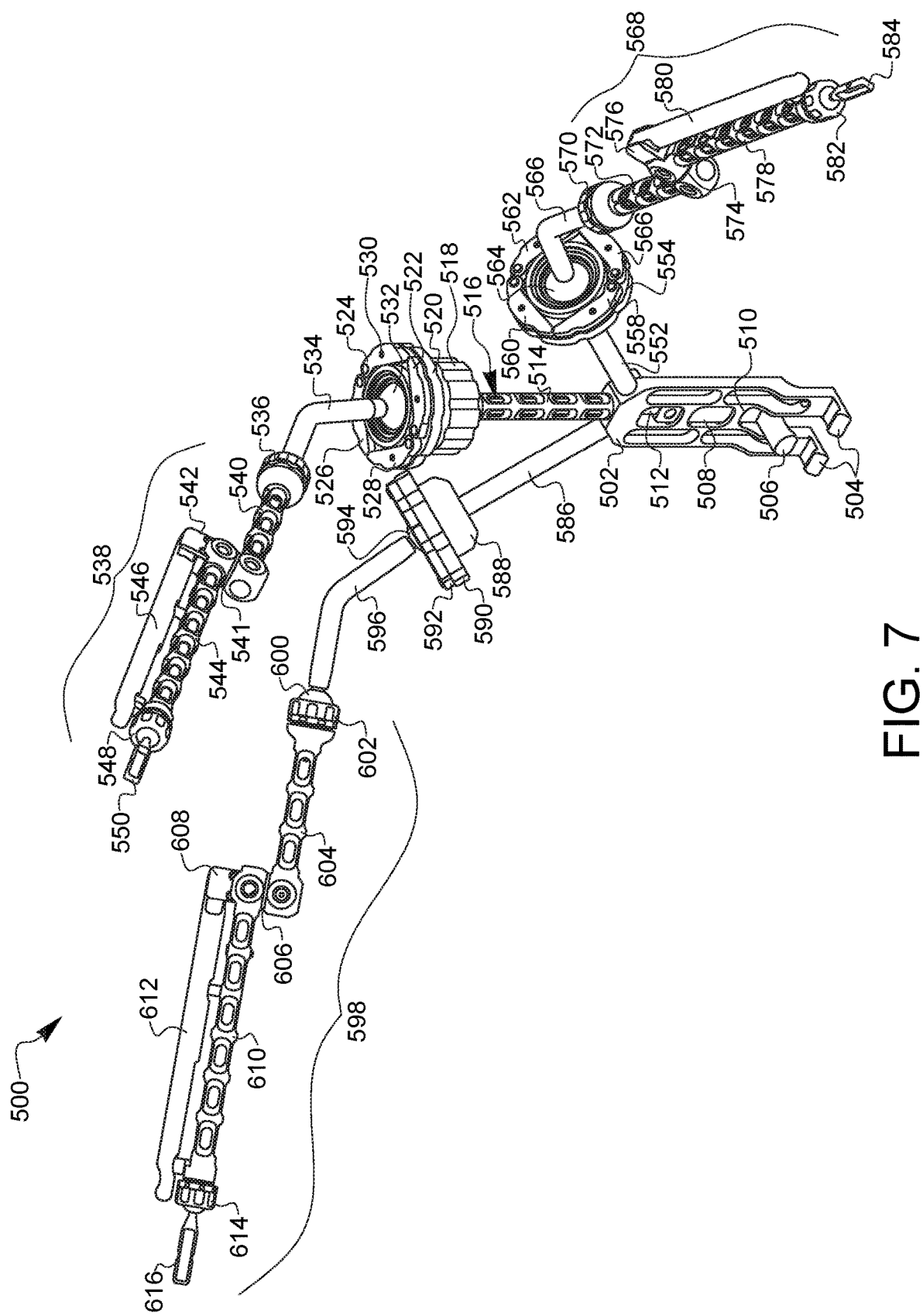
FIG. 7 is a top-right-front perspective view of another embodiment of a surgical equipment holder dock.

FIG. 7 is a top-right-front perspective view of another embodiment of a surgical equipment holder dock. This embodiment of a surgical equipment holder dock 500 includes a base 502 which defines a pair of lower clamp jaws 504 and a lower stop 510. Internally movable within the base 502 of the surgical equipment holder dock 500 is an upper clamp jaw 506 coupled to an upper clamp jaw shaft, connected to an inner rod 512. The inner rod 512 is disposed internally in the base 502, and movably held within a central docking arm 514, which is connected to the base 502. The inner rod is rotatably coupled to the upper clamp jaw. The central attachment nut 520 is configured to limit the vertical travel of the upper clamp jaw shaft 508 and therefore the relative position of the upper clamp jaw 506 in relation to the lower clamp jaws 504. Other embodiments may or may not include stop pins and may limit travel of the movable portion of the clamp jaws by means known to those skilled in the arts. Other embodiments may have a movable lower clamp jaws or movable lower and upper clamp jaws. The base 502 is configured to clamp the surgical equipment holder dock 500 to a surgical table rail. Attached to the upper portion of the base 502 is a central docking arm 514. This central docking arm 514 defines several cleaning features to facilitate cleaning and disinfecting the dock, including internal components and surfaces subsequent to use in surgical settings. Other arms within this embodiment have similar features. The central docking arm 514 is coupled to a knob 518. The knob 518 is coupled to the inner rod 512 and therefore the upper clamp jaw shaft 508. The mechanism of this action will be discussed later. Above the knob 518 is a central ball cup, not shown in this view, but has been described previously in regard to other embodiments. A central attachment nut 520 is coupled to the central ball cup. The attachment nut 520 includes four extendable moment arms 522, 524, 526, 528 pivotably coupled to the attachment nut 520. Each of the extendable moment arms 522, 524, 526, 528 has a biased retention feature 530 configured to keep the extendable moment arms 522, 524, 526, 528 retracted until they are intentionally extended. A large coupler ball 532 is held between the central ball cup attached to the central docking arm 514 and the attachment nut 520. A bent coupler rod 534 is attached on one end to the large coupler ball 532 and attached to a small coupler ball, not shown here, on the opposite end. Over the small coupler ball a retainer ring 536 is connected, which will later serve as a mounting point for a surgical equipment holder 538. The central surgical equipment holder arm assembly 538 has a first arm 540 attached to the retainer ring 536, a locking joint 541 which joins a second arm 544 to the first arm 540. A lever block 542 having an operating lever 546 is located at the top of the locking joint 541. The second arm 544 also has an end joint 548 which includes an end effector 550. The end effector 550 is an attachment point for attaching any number of surgical equipment to the end of the central surgical equipment holder arm assembly 538. In this configuration, a piece of surgical equipment, would be easily repositionable by adjusting the central surgical equipment holder arm assembly 538. The operating lever 546 is configured to lock and unlock the joints of the central surgical equipment holder arm assembly 538 at the position of the retainer ring 536, locking joint 541 and end joint 548, allowing the joint to move freely when unlocked, and holding the joint at the retainer ring 536, locking joint 541, and end joint 548 in a locked position, therefore keeping the relative positions of the first arm 540, second arm 544, and end effector 550 in a fixed position when locked.

In addition to the central docking arm 514, the surgical equipment holder dock 400 also has a first side docking arm 552 and a second side docking arm 586 attached to the base 502, each angled at an approximate angle of 45-degrees relative to the central docking arm 514. While a 45-degree angle is shown in this embodiments, other embodiments may have other angles of the side arm as compared to the central docking arm 514. The first side docking arm 552 and accompanying assembly has a similar structure to that of the previously described structure of the central docking arm 514 and central surgical equipment holder arm assembly 538. There is a first side ball cup, not shown in this view, coupled to the first side docking arm 552. Coupled to the first side ball cup is a first side attachment nut 554 which similar to previously described embodiments and attachment nut 520, has four extendable moment arms 556, 558, 560, 562. Movably held between the first side ball cup and the attachment nut 520 is a ball 564 coupled to a first side coupling rod 566. A small coupler ball (not visible here) and retainer ring 570, which are coupled to the opposite end of the first side coupling rod 566 are fastened to a first side surgical equipment holder arm assembly 568. The first side surgical equipment holder arm assembly 568 has a first arm 572 attached to the retainer ring 570, a locking joint 574 which joins the second arm 578 to the first arm 572. A lever block 576 having an operating lever 580 is located at the top of the locking joint 574. The second arm 578 has an end joint 582 which includes a pivotable end effector 584. The end effector 584 is an attachment point for attaching any number of surgical equipment to the end of the first side surgical equipment holder arm assembly 568. In this configuration, a piece of surgical equipment, would be easily repositionable by adjusting the first side surgical equipment holder arm assembly 568. The operating lever 580 is configured, when engaged or released, to lock and unlock the joints of the first side surgical equipment holder arm assembly 568 at the small coupler ball, locking joint 574 and end joint 582, allowing the joint and arms to move freely when unlocked, and holding the small coupler ball, locking joint 574, and end joint 582 in a locked position, therefore keeping the relative positions of the first arm 572, second arm 578, and end effector 584 in a fixed position when engaged and locked.

The second side docking arm 586 and accompanying assembly has a similar structure to that of the previously described structure of the central docking arm 514 and central surgical equipment holder arm assembly 538. There is a second side ball cup 588 coupled to the second side docking arm 586. Coupled to the second side ball cup 588 is a second side attachment nut 590 which similar to previously described embodiments and attachment nut 520, has four extendable moment arms 592, only one of which is visible in this view. Movably held between the second side ball cup 588 and the second side attachment nut 590 is a ball 594 which is coupled to a second side coupler rod 596. A small coupler ball 600 and retainer ring 602, which are coupled to the opposite end of the second side coupler rod 596 are fastened to a second side surgical equipment holder arm assembly 598. The second side surgical equipment holder arm assembly 598 has a first arm 604 attached to the retainer ring 602, a locking joint 606 which joins the second arm 610 to the first arm 604. A lever block 608 having an operating lever 612 is located at the top of the locking joint 606 The second arm 610 has an end joint 614 which includes a pivotable end effector 616. The end effector 616 is an attachment point for attaching any number of surgical equipment to the end of the second side surgical equipment holder arm assembly 598. In this configuration, a piece of surgical equipment, would be easily repositionable by adjusting the second side surgical equipment holder arm assembly 598. The operating lever 612 is configured, when engaged or released, to lock and unlock the joints of the second side surgical equipment holder arm assembly 598 at the small coupler ball 600, locking joint 606 and end joint 614, allowing the joint and arms to move freely when unlocked, and holding the small coupler ball 600, locking joint 606, and end joint 614 in a locked position, therefore keeping the relative positions of the first arm 604, second arm 610, and end effector 616 in a fixed position when engaged and locked.

Figure 8:
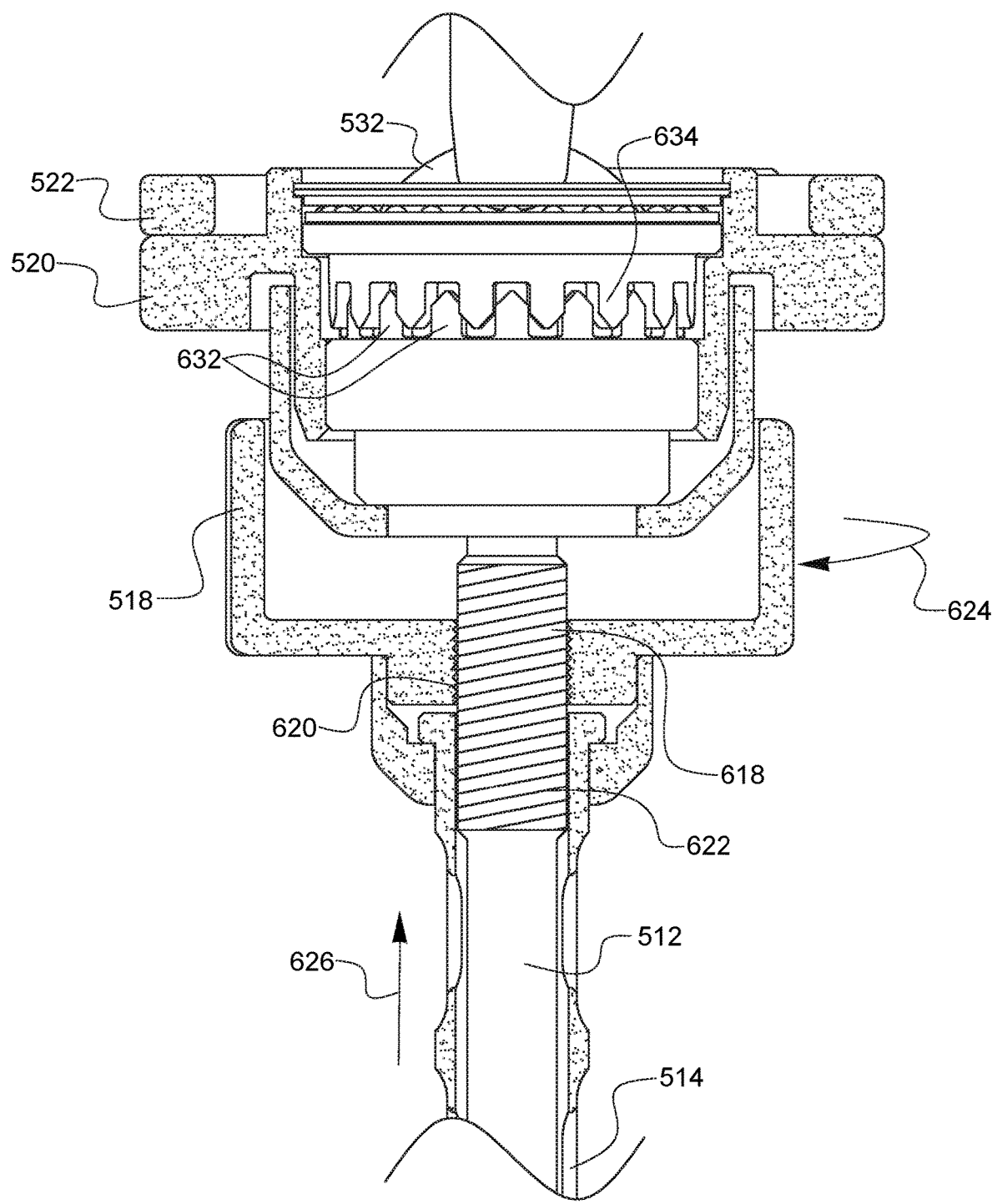
FIG. 8 is a partial cross-sectional view of the surgical equipment holder dock of FIG. 7.

FIG. 8 is a partial cross-sectional view of the surgical equipment holder dock of FIG. 7. FIG. 8 is directed to the knob 518 and central attachment nut 520 portion of the central docking arm 514 portion of the surgical equipment holder dock of FIG. 7. The knob 518 defines an inner circumference having mechanical threading, or threads 620. Also illustrated is the inner rod 512 which is free to rotate within the central docking arm 514. A portion of the inner rod 512 also defines mechanical threading, or threads 622 on an outer circumference of the inner rod 512. When the knob 518 is rotated or turned in direction 624, the threading 522 of the inner rod 512 and the threading 520 of the knob 518 intermesh to drive the inner rod 512 in an upward direction 626. As the inner rod 512 is rotatably coupled to the upper clamp jaw shaft 508 and the upper clamp jaw 506, the upper clamp jaw 506 is therefore pulled upwards in direction 626 as the knob 518 is rotated in direction 624. This rotation as described increases the distance between the upper jaw and the lower clamping jaw, allowing the base 502 portion of the surgical equipment holder dock 500 to be loosened and either removed from a table rail, or the jaws separated to a sufficient extent such that the base 502 portion of the surgical equipment holder dock 500 can be placed onto a rail of an operating table or similar rail. When rotating knob 518 in the opposite direction, the distance between the upper jaw and the lower clamping jaw is decreased. This allows the base 502 portion of the surgical equipment holder dock 500 to be tightened and clamped onto a table rail such that the base 502 portion of the surgical equipment holder dock 500 can be firmly held onto a rail of an operating table or similar rail.

Figure 9:
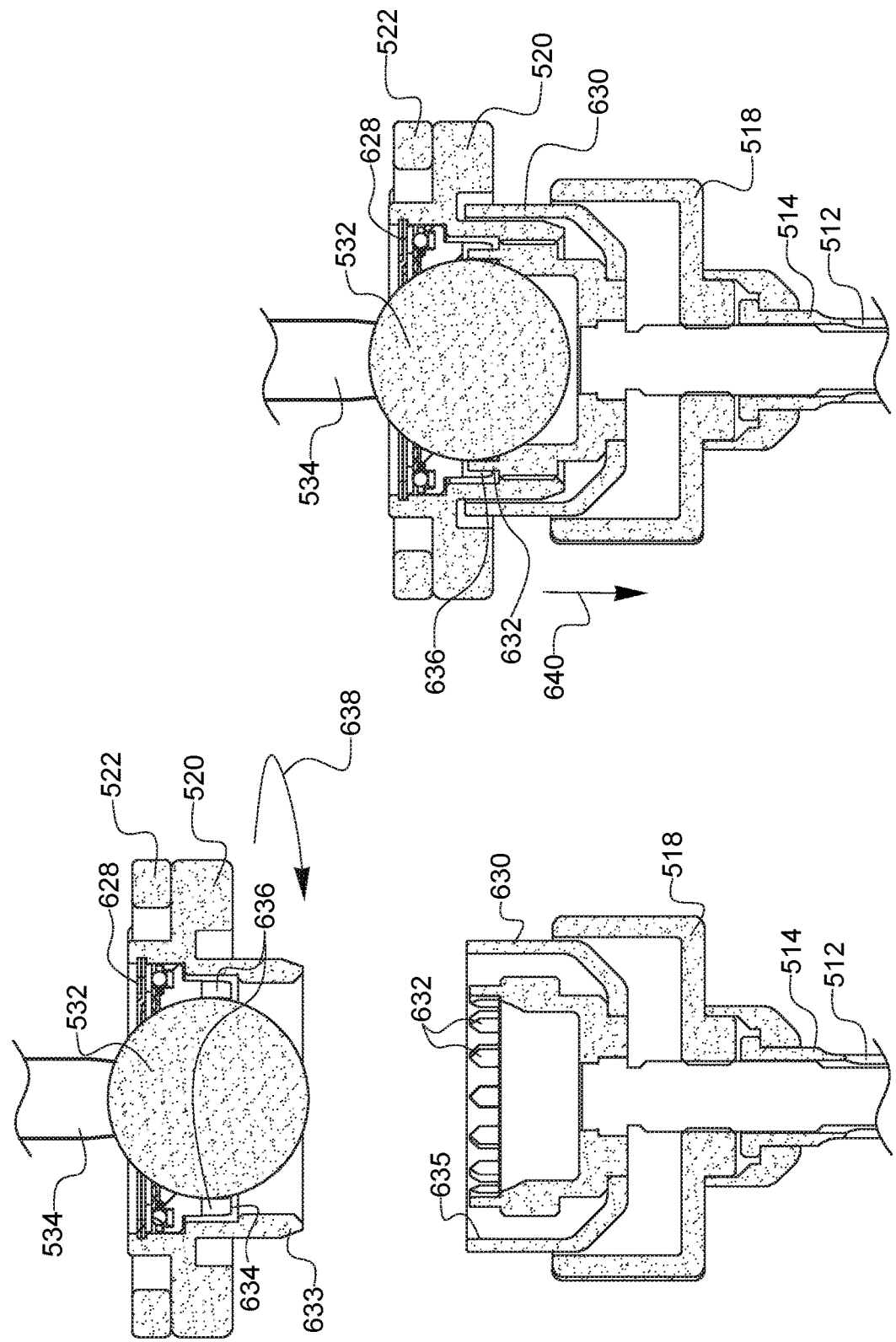
FIGS. 9A and 9B are partial cross-sectional views of the surgical equipment holder dock of FIG. 7.

FIGS. 9A and 9B are partial cross-sectional views of the surgical equipment holder dock of FIG. 7. FIG. 9A illustrates a the view of the knob 518 and central attachment nut 520 portion of the central docking arm 514 portion of the surgical equipment holder dock of FIG. 7. As shown in the central attachment nut 520, a retaining assembly 628 is held captive in the central attachment nut 520 and constrains the large coupler ball 532 and the attached coupler rod 534 from being removed from the top of the central attachment nut 520. Surrounding the ball and also held captive in the central attachment nut 520 is an upper crenulation ring 634 which defines several upper interdigitating features 636. These upper interdigitating features 636 are structured as spaced blunted spikes or rectangular, peaked fingers that assist in aligning and interlocking the central attachment nut 520 when fully attached to the ball cup 630 portion of the surgical equipment holder dock 500. The ball cup 630 also includes several lower interdigitating features 632 in the center portion of the ball cup 630. These interdigitating features 632 are structured as spaced blunted spikes or rectangular, peaked fingers that assist in aligning and interlocking the ball cup 630 when the central attachment nut 520 is attached to the ball cup 630. When the central attachment nut 520 is placed onto the ball cup 630 and rotated in direction 638, there are threads 633 defined by the outer wall of the central attachment nut 520 that intermesh with corresponding threads 635 defined by an inner wall of the ball cup 630. As the central attachment nut 520 is tightened onto the ball cup 630, the ball 532, and therefore the attached coupler rod 534 and accompanying surgical equipment holder is at first movable, pivotable, and captive between the central attachment nut 520 and the ball cup 630. As the central attachment nut 520 is tightened further, at times with the assistance of the extended extendable moment arms, the shapes of the upper interdigitating features 636 on the central attachment nut 520 and the interdigitating features 632 on the ball cup 630 are complementary and correspond to one another such that they interlock as the central attachment nut 520 is further tightened onto the ball cup 630. As shown in FIG. 9B, as the central attachment nut 520 moves in direction 640, the rotational force of tightening central attachment nut 520 is translated into vertical tension in direction 640, the large coupler ball 532 and therefore the coupler rod 534 and accompanying surgical equipment holder is held immobile and in a fixed position until such time that the central attachment nut 520 is once again loosened. The interlocked and interdigitating nature of the upper interdigitating features 636 on the central attachment nut 520 and the interdigitating features 632 on the ball cup 630 helps align and preserve position of a surgical equipment holder, and therefore an attached surgical tool or piece of surgical equipment. Maintaining a constant and consistent position of surgical tools and equipment is improved with the use of an attachment feature as described herein. An additional view of this interlocking feature in a fully tightened configuration is illustrated in FIG. 8 as well. While the interdigitating features 632, 636 shown herein have a particular shape and spacing, other possible shapes and spacings known to those skilled in the art may be used in alternate embodiments.

Figure 10:
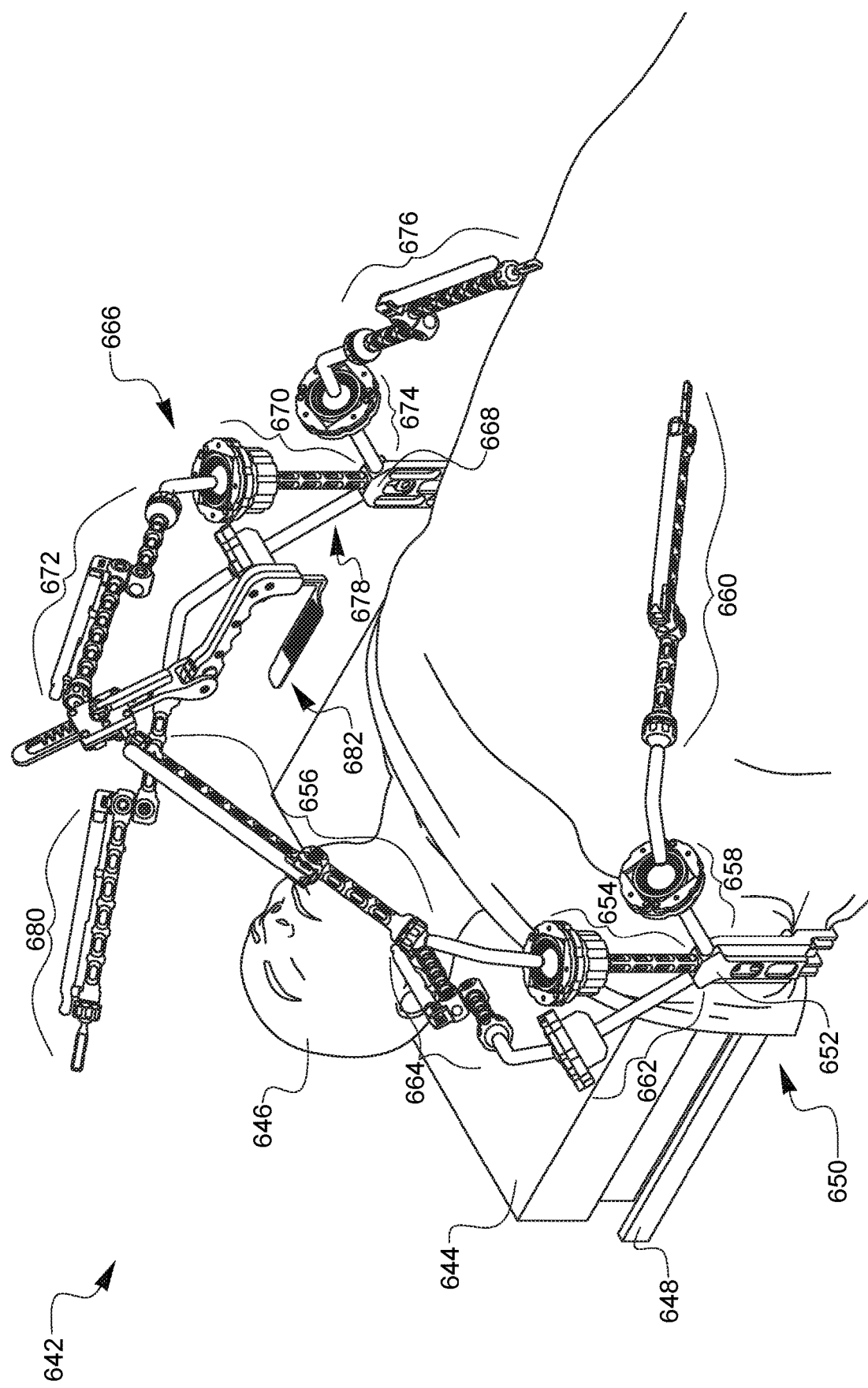
FIG. 10 is a perspective view of two surgical equipment holder docks of FIG. 7 attached to a surgical table with various adapters and equipment attached thereto.

FIG. 10 is a perspective view of two surgical equipment holder docks of FIG. 7 attached to a surgical table with various adapters and equipment attached thereto. In the illustrated surgical setting 642, an operating table 644 having a rail 648 and a patient 646 on the table 644 prepared for a surgical procedure are shown. Positioned on the rail 648 is a first surgical equipment holder dock 650 with its first base 652 clamped onto the rail 648. The first surgical equipment holder dock 650 has a central dock 654 and accompanying central surgical equipment holder 656 attached to the first base 652. The first surgical equipment holder dock 650 also has a first side dock 658 and first side surgical equipment holder 660 attached to a first side of the first base 652, and a second side dock 662 and a second side surgical equipment holder 664 attached to a second side of the first base 652. Each of the first side surgical equipment holder 660 and second side surgical equipment holder 664 can be utilized to position and hold one or more pieces of surgical equipment or tools such as scope holders, cannulas, or other surgical implements during a minimally invasive or other surgical procedure. Positioned on a rail, not shown in this view, on the opposite side of the operating table 644 is a second surgical equipment holder dock 666 with a second base 668 clamped onto the opposing rail. The second surgical equipment holder dock 666 has a central dock 670 and accompanying central surgical equipment holder 672 attached to the second base 668. The second surgical equipment holder dock 666 also has a first side dock 674 and first side surgical equipment holder 676 attached to a first side of the second base 668, and a second side dock 678 and a second surgical equipment holder 680 attached to a second side of the second base 668. Each of the first side surgical equipment holder 676 and second side surgical equipment holder 680 can be utilized to position and hold one or more pieces of surgical equipment or tools such as scope holders, cannulas, or other surgical implements during a minimally invasive or other surgical procedure. In this configuration, the central surgical equipment holder 656 and central surgical equipment holder 672 are shown bridging over the first side docking arm 64 in order to firmly position a surgical equipment 682 in a centralized location relative to the patient 646 on the table 644. While this is one configuration shown, the adjustability and versatility of a single or multiple surgical equipment holder docks as shown and described herein provides a number of variable and repositionable configurations for surgical equipment and surgical equipment holders providing numerous approaches to providing more efficient and consistent holding and positioning of surgical instrumentation to assist surgeons and surgical teams in performing a variety of minimally invasive surgical procedures and techniques.

Various advantages of a surgical equipment holder have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A dock for a surgical equipment holder, comprising:
   a base comprising:
      a central arm mount;
      a side arm mount; and
      a lower clamping jaw;
   an upper jaw movably coupled to the base; and
   a central docking arm coupled to the central arm mount comprising:
      an inner rod coupled to the upper jaw;
      a knob coupled to the inner rod;
      a hollow outer rod disposed over the inner rod; and
      a central ball cup coupled to the inner rod; and
   an attachment nut coupled to the central ball cup.

2. The dock for a surgical equipment holder of claim 1, further comprising a ball pivotably held between the central ball cup and the attachment nut.

3. The dock for a surgical equipment holder of claim 2, further comprising the surgical equipment holder coupled to the ball.

4. The dock for a surgical equipment holder of claim 1, further comprising an extendable moment arm coupled to the attachment nut.

5. The dock for a surgical equipment holder of claim 1, wherein the side arm mount further comprises a side docking arm and a first side ball cup coupled to the side docking arm.

6. The dock for a surgical equipment holder of claim 5, further comprising a first side attachment nut coupled to the first side ball cup.

7. The dock for a surgical equipment holder of claim 6, further comprising a ball pivotably held between the first side ball cup and the first side attachment nut.

8. The dock for a surgical equipment holder of claim 7, further comprising the surgical equipment holder coupled to the ball.

9. The dock for a surgical equipment holder of claim 6, further comprising an extendable moment arm coupled to the first side attachment nut.

10. The dock for a surgical equipment holder of claim 1, wherein the base further comprises a second side arm mount.

11. The dock for a surgical equipment holder of claim 10, wherein the second side arm mount further comprises a side docking arm and a second side ball cup coupled to the side docking arm.

12. The dock for a surgical equipment holder of claim 11, further comprising a second side attachment nut coupled to the second side ball cup.

13. The dock for a surgical equipment holder of claim 12, further comprising a ball pivotably held between the second side ball cup and the second side attachment nut.

14. The dock for a surgical equipment holder of claim 13, further comprising the surgical equipment holder coupled to the ball.

15. The dock for a surgical equipment holder of claim 12, further comprising an extendable moment arm coupled to the second side attachment nut.

16. The dock for a surgical equipment holder of claim 1, wherein:
- a portion of the inner rod coupled to the knob further comprises threading; and
- a portion of the knob coupled to the inner rod further comprises threading that intermeshes with the threading on the inner rod.

17. The dock for a surgical equipment holder of claim 16, wherein the inner rod is rotatably coupled to the upper jaw.

18. The dock for a surgical equipment holder of claim 17, configured such that:
- when rotating the knob in a first direction, a distance between the upper jaw and the lower clamping jaw is increased; and
- when rotating the knob in a second direction, the distance between the upper jaw and the lower clamping jaw is decreased.

19. The dock for a surgical equipment holder of claim 1, wherein the central ball cup further comprises a plurality of interdigitating features and the attachment nut further comprises a plurality of interdigitating features corresponding to the plurality of interdigitating features on the central ball cup.

20. The dock for a surgical equipment holder of claim 19, configured such that when the plurality of interdigitating features on the central ball cup and the plurality of interdigitating features on the attachment nut interlock when the attachment nut is tightened onto the central ball cup.

21. A dock for a surgical equipment holder, comprising:
- a base comprising:
  - a central arm mount;
  - a first side arm mount;
  - a second side arm mount; and
  - a lower clamping jaw;
- an upper jaw movably coupled to the base; and
- a central docking arm coupled to the central arm mount comprising:
  - an inner rod coupled to the upper jaw;
  - a knob coupled to the inner rod;
  - a hollow outer rod disposed over the inner rod; and
  - a central ball cup coupled to the inner rod;
- a central attachment nut having an extendable moment arm;
- a ball pivotably held between the central ball cup and the central attachment nut; and
- the surgical equipment holder wherein said surgical equipment holder coupled to the ball.

* * * * *